US010064355B2

(12) United States Patent
Linscombe

(10) Patent No.: US 10,064,355 B2
(45) Date of Patent: Sep. 4, 2018

(54) RICE CULTIVAR DESIGNATED 'CL271'

(71) Applicant: Steven D. Linscombe, Crowley, LA (US)

(72) Inventor: Steven D. Linscombe, Crowley, LA (US)

(73) Assignee: Board of Supervisors of Louisiana State University and Agricultural and Mechanical College, Baton Rouge, LA (US)

( * ) Notice: Subject to any disclaimer, the term of this patent is extended or adjusted under 35 U.S.C. 154(b) by 0 days.

(21) Appl. No.: 15/102,467

(22) PCT Filed: Dec. 8, 2014

(86) PCT No.: PCT/US2014/068983
§ 371 (c)(1),
(2) Date: Jun. 7, 2016

(87) PCT Pub. No.: WO2015/088933
PCT Pub. Date: Jun. 18, 2015

(65) Prior Publication Data
US 2016/0309673 A1    Oct. 27, 2016

Related U.S. Application Data

(60) Provisional application No. 61/913,451, filed on Dec. 9, 2013.

(51) Int. Cl.
| | | |
|---|---|---|
| *A01H 5/00* | (2018.01) | |
| *A01H 6/00* | (2018.01) | |
| *A01H 5/10* | (2018.01) | |
| *A01G 22/22* | (2018.01) | |
| *A01H 1/02* | (2006.01) | |
| *A01N 43/50* | (2006.01) | |
| *A01N 47/30* | (2006.01) | |
| *C12N 15/82* | (2006.01) | |

(52) U.S. Cl.
CPC ............... *A01H 5/10* (2013.01); *A01G 22/22* (2018.02); *A01H 1/02* (2013.01); *A01N 43/50* (2013.01); *A01N 47/30* (2013.01); *C12N 15/8241* (2013.01); *C12N 15/8245* (2013.01); *C12N 15/8247* (2013.01); *C12N 15/8274* (2013.01); *C12N 15/8278* (2013.01); *C12N 15/8279* (2013.01); *C12N 15/8281* (2013.01); *C12N 15/8282* (2013.01); *C12N 15/8283* (2013.01); *C12N 15/8286* (2013.01); *C12N 15/8289* (2013.01)

(58) Field of Classification Search
None
See application file for complete search history.

(56) References Cited

U.S. PATENT DOCUMENTS

| | | | |
|---|---|---|---|
| 5,545,822 A | 8/1996 | Croughan | 800/300 |
| 5,605,011 A | 2/1997 | Bedbrook et al. | 47/58.1 R |
| 5,736,629 A | 4/1998 | Croughan | 800/300 |
| 5,773,703 A | 6/1998 | Croughan | 800/300 |
| 5,773,704 A | 6/1998 | Croughan | 800/300 |
| 5,952,553 A | 9/1999 | Croughan | 800/320.2 |
| 6,274,796 B1 | 8/2001 | Croughan | 800/320.2 |
| 6,911,589 B2 | 3/2005 | Johnson | 800/278 |
| 6,943,280 B2 | 9/2005 | Croughan | 800/300 |
| 7,019,196 B1 | 3/2006 | Croughan | 800/300 |
| 7,345,221 B2 | 3/2008 | Croughan | 800/300 |
| 7,399,905 B2 | 7/2008 | Croughan | 800/300 |
| 7,495,153 B2 | 2/2009 | Croughan | 800/260 |
| 7,754,947 B2 | 7/2010 | Croughan | 800/300 |
| 7,786,360 B2 | 8/2010 | Linscombe | 800/320.2 |
| 2006/0162016 A1 | 7/2006 | Croughan | 800/278 |
| 2007/0061915 A1 | 3/2007 | Linscombe | 800/260 |
| 2009/0025108 A1 | 1/2009 | Croughan | 800/320.2 |
| 2010/0257623 A1 | 10/2010 | Croughan | 800/260 |
| 2011/0232247 A1 | 9/2011 | Zhu et al. | 56/1 |
| 2012/0204285 A1* | 8/2012 | Linscombe | A01H 5/10 800/260 |

FOREIGN PATENT DOCUMENTS

| | | |
|---|---|---|
| WO | WO 2010/059656 | 5/2010 |
| WO | WO 2011/044315 | 4/2011 |
| WO | WO 2011/044334 | 4/2011 |
| WO | WO 2012/135558 | 10/2012 |

OTHER PUBLICATIONS

"LSU Ag Center Looking at Three Promising Rice Varieties for 2014, 2015." *Delta Farm Press*: n. pag. Dec. 8, 2013. Web.
Penton Media (Producer). (Dec. 8, 2013). LSU Ag Center Looking at Three Promising Rice Varieties for 2014, 2015 [Video File]. Retrieved from http://deltafarmpress.com/rice/lsu-ag-center-looking-three-promising-rice-varieties-2014-2015.

* cited by examiner

Primary Examiner — Medina Ahmed Ibrahim
(74) Attorney, Agent, or Firm — John H. Runnels

(57) ABSTRACT

The herbicide-tolerant rice cultivar designated 'CL271' and its hybrids and derivatives are disclosed.

52 Claims, No Drawings

RICE CULTIVAR DESIGNATED 'CL271'

This is the United States national stage of international application PCT/US2014/068983, international filing date Dec. 8, 2014, which claims the benefit of the Dec. 9, 2013 filing date of U.S. provisional patent application Ser. No. 61/913,451 under 35 U.S.C. § 119(e).

TECHNICAL FIELD

This invention pertains to the rice cultivar designated 'CL271,' and to hybrids of, and cultivars derived from the rice cultivar designated 'CL271.'

BACKGROUND ART

Rice is an ancient agricultural crop, and remains one of the world's principal food crops. There are two cultivated species of rice: *Oryza sativa* L., the Asian rice, and *O. glaberrima* Steud., the African rice. *Oryza sativa* L. constitutes virtually all of the world's cultivated rice and is the species grown in the United States. The three major rice producing regions in the United States are the Mississippi Delta (Arkansas, Mississippi, northeast Louisiana, southeast Missouri), the Gulf Coast (southwest Louisiana, southeast Texas); and the Central Valley of California. See generally U.S. Pat. No. 6,911,589.

Rice is a semiaquatic crop that benefits from flooded soil conditions during part or all of the growing season. In the United States, rice is typically grown on flooded soil to optimize grain yields. Heavy clay soils or silt loam soils with hard pan layers about 30 cm below the surface are typical rice-producing soils, because they reduce water loss from soil percolation. Rice production in the United States can be broadly categorized as either dry-seeded or water-seeded. In the dry-seeded system, rice is sown into a well-prepared seed bed with a grain drill or by broadcasting the seed and incorporating it with a disk or harrow. Moisture for seed germination comes from irrigation or rainfall. Another method of dry-seeding is to broadcast the seed by airplane into a flooded field, and then promptly drain the water from the field. For the dry-seeded system, when the plants have reached sufficient size (four- to five-leaf stage), a shallow permanent flood of water 5 to 16 cm deep is applied to the field for the remainder of the crop season. Some rice is grown in upland production systems, without flooding.

One method of water-seeding is to soak rice seed for 12 to 36 hours to initiate germination, and then to broadcast the seed by airplane into a flooded field. The seedlings emerge through a shallow flood, or the water may be drained from the field for a short time to enhance seedling establishment. A shallow flood is then maintained until the rice approaches maturity. For both the dry-seeded and water-seeded production systems, the fields are drained when the crop is mature, and the rice is harvested 2 to 3 weeks later with large combines.

In rice breeding programs, breeders typically use the same production systems that predominate in the region. Thus, a drill-seeded breeding nursery is typically used by breeders in a region where rice is drill-seeded, and a water-seeded nursery is typically used in regions where water-seeding prevails.

Rice in the United States is classified into three primary market types by grain size, shape, and endosperm composition: long-grain, medium-grain, and short-grain. Typical U.S. long-grain cultivars cook dry and fluffy when steamed or boiled, while medium- and short-grain cultivars cook moist and sticky. Medium grain rice is usually slightly wider than long grain rice and slightly shorter, with a length:width ratio between 2:1 and 3:1.

In the early 1980's about two thirds of Louisiana rice acreage was planted with medium grain cultivars. Market demand and the release of superior long grain varieties (e.g., superior yield and superior disease resistance) caused medium-grain plantings to decline considerably over the last 25 years or so. By the mid-1990s, Louisiana rice acreage was planted 65 percent long grains, and 35 percent medium grains. For the past 10 years or so, less than 5 percent of Louisiana rice acreage has been medium grains.

Long-grain cultivars have become the principal varieties grown, not just in Louisiana, but throughout the southern United States in recent years. However, there does remain demand for medium grain production in the region, and recently that demand has increased substantially. While there are several non-herbicide-resistant, medium-grain cultivars available for the region, such as 'Jupiter,' Neptune; and 'Bengal,' only one herbicide-resistant, medium grain rice cultivar has previously been released, namely 'CL261.' See United States patent application publication no. 2012/0204285.

There is an unfilled need for new herbicide-resistant, medium-grain rice cultivars, particularly those that are well-adapted for growing conditions in the southern United States. Medium grain rice is more common in California, but Southern U.S. medium grains differ somewhat from those grown in California. Additionally, the weed called "red rice" has been a substantial problem in medium grain rice fields in the southern United States.

Although specific breeding objectives vary somewhat in different regions, increasing yield is a primary objective in all programs. Grain yield depends, in part, on the number of panicles per unit area, the number of fertile florets per panicle, and grain weight per floret. Increases in any or all of these components may help improve yields. Heritable variation exists for each of these components, and breeders may directly or indirectly select for any of them.

There are numerous steps in the development of any novel, desirable plant germplasm. Plant breeding begins with the analysis and definition of problems and weaknesses of the current germplasm, the establishment of program goals, and the definition of specific breeding objectives. The next step is selection (or generation) of germplasm that possesses the desired traits to meet the program goals. A goal is often to combine in a single variety an improved combination of desirable traits from two or more ancestral germplasm lines. These traits may include such things as higher seed yield, resistance to disease or insects, better stems and roots, tolerance to low temperatures, and better agronomic characteristics or grain quality.

The choice of breeding and selection methods depends on the mode of plant reproduction, the heritability of the trait(s) being improved, and the type of seed that is used commercially (e.g., $F_1$ hybrid, versus pure line or inbred cultivars). For highly heritable traits, a choice of superior individual plants evaluated at a single location may sometimes be effective, while for traits with low or more complex heritability, selection is often based on mean values obtained from replicated evaluations of families of related plants. Selection methods include pedigree selection, modified pedigree selection, mass selection, recurrent selection, and combinations of these methods.

The complexity of inheritance influences the choice of breeding method. Backcross breeding is used to transfer one or a few favorable genes for a highly heritable trait into a desirable cultivar. This approach has been used extensively for breeding disease-resistant cultivars. Various recurrent selection techniques are used to improve quantitatively-inherited traits controlled by numerous genes. The use of recurrent selection in self-pollinating crops depends on the ease of pollination, the frequency of successful hybrids from each pollination, and the number of hybrid offspring from each successful cross.

Promising advanced breeding lines are thoroughly tested and compared to appropriate standards in environments representative of the commercial target area(s), typically for three or more years. The best lines become candidates for new commercial cultivars; those still deficient in a few traits may be used as parents to produce new populations for further selection.

These processes, which lead ultimately to marketing and distribution of new cultivars or hybrids, typically take 8 to 12 years from the time of the first cross; they may further rely on (and be delayed by) the development of improved breeding lines as precursors. Development of new cultivars and hybrids is a time-consuming process that requires precise forward planning and efficient use of resources. There are never assurances of a successful outcome.

A particularly difficult task is the identification of individual plants that are, indeed, genetically superior. A plant's phenotype results from a complex interaction of genetics and environment. One method for identifying a genetically superior plant is to observe its performance relative to other experimental plants and to a widely grown standard cultivar raised in an identical environment. Repeated observations from multiple locations can help provide a better estimate of genetic worth.

The goal of rice breeding is to develop new, unique, and superior rice cultivars and hybrids. The breeder initially selects and crosses two or more parental lines, followed by self-pollination and selection, producing many new genetic combinations. The breeder can generate billions of different genetic combinations via crossing, selfing, and mutation breeding. The traditional breeder has no direct control of genetics at the molecular level. Therefore, two traditional breeders working independently of one another will never develop the same line, or even very similar lines, with the same traits.

Each year, the plant breeder selects germplasm to advance to the next generation. This germplasm is grown under different geographical, climatic, and soil conditions. Further selections are then made, during and at the end of the growing season. The resulting cultivars (or hybrids) and their characteristics are inherently unpredictable. This is because the traditional breeder's selection occurs in unique environments, with no control at the molecular level, and with potentially billions of different possible genetic combinations being generated. A breeder cannot predict the final resulting line, except possibly in a very gross and generic fashion. Further, the same breeder may not produce the same cultivar twice, even starting with the same parental lines, using the same selection techniques. This uncontrollable variation results in substantial effort and expenditures in developing superior new rice cultivars (or hybrids); and makes each new cultivar (or hybrid) novel and unpredictable.

The selection of superior hybrid crosses is conducted slightly differently. Hybrid seed is typically produced by manual crosses between selected male-fertile parents or by using genetic male sterility systems. These hybrids are typically selected for single gene traits that unambiguously indicate that a plant is indeed an $F_1$ hybrid that has inherited traits from both presumptive parents, particularly the male parent (since rice normally self-fertilizes). Such traits might include, for example, a semi dwarf plant type, pubescence, awns, or apiculus color. Additional data on parental lines, as well as the phenotype of the hybrid, influence the breeder's decision whether to continue with a particular hybrid cross or an analogous cross, using related parental lines.

Pedigree breeding and recurrent selection breeding methods are sometimes used to develop cultivars from breeding populations. These breeding methods combine desirable traits from two or more cultivars or other germplasm sources into breeding pools from which cultivars are developed by selfing and selection of desired phenotypes. The new cultivars are evaluated to determine commercial potential.

Pedigree breeding is often used to improve self-pollinating crops. Two parents possessing favorable, complementary traits are crossed to produce $F_1$ plants. An $F_2$ population is produced by selfing one or more $F_1$s. Selection of the superior individual plants may begin in the $F_2$ (or later) generation. Then, beginning in the $F_3$ (or other subsequent) generation, individual plants are selected. Replicated testing of panicle rows from the selected plants can begin in the $F_4$ (or other subsequent) generation, both to fix the desired traits and to improve the effectiveness of selection for traits that have low heritability. At an advanced stage of inbreeding (e.g., $F_6$ or $F_7$), the best lines or mixtures of phenotypically-similar lines are tested for potential release as new cultivars.

Mass and recurrent selection methods can also be used to improve populations of either self- or cross-pollinating crops. A genetically variable population of heterozygous individuals is either identified or created by intercrossing several different parents. The best offspring plants are selected based on individual superiority, outstanding progeny, or excellent combining ability. The selected plants are intercrossed to produce a new population in which further cycles of selection are continued.

Backcross breeding is often used to transfer genes for a simply inherited, highly heritable trait into a desirable homozygous cultivar or inbred line, which is the recurrent parent. The source of the trait to be transferred is called the donor parent. The resulting plant should ideally have the attributes of the recurrent parent (e.g., cultivar) and the desired new trait transferred from the donor parent. After the initial cross, individuals possessing the desired donor phenotype (e.g., disease resistance, insect resistance, herbicide tolerance) are selected and repeatedly crossed (backcrossed) to the recurrent parent.

The single-seed descent procedure in the strict sense refers to planting a segregating population, harvesting a sample of one seed per plant, and using the one-seed sample to plant the next generation. When the population has been advanced from the $F_2$ generation to the desired level of inbreeding, the several plants from which the lines are derived will each trace to different $F_2$ individuals. The number of plants in a population declines each generation due to failure of some seeds to germinate or the failure of some plants to produce at least one seed. As a result, not all of the $F_2$ plants originally sampled in the population will be represented by progeny in subsequent generations.

In a multiple-seed procedure, the breeder harvests one or more seeds from each plant in a population and threshes them together to form a bulk. Part of the bulk is used to plant the next generation and part is held in reserve. The procedure has been referred to as modified single-seed descent or the pod-bulk technique. The multiple-seed procedure has been used to save labor at harvest. It is considerably faster to thresh panicles by machine than to remove one seed from each by hand as in the single-seed procedure. The multiple-seed procedure also makes it possible to plant the same number of seeds from a population for each generation of inbreeding. Enough seeds are harvested to compensate for plants that did not germinate or produce seed.

Other common and less-common breeding methods are known and used in the art. See, e.g., R. W. Allard, Principles of Plant Breeding (John Wiley and Sons, Inc., New York, N.Y., 1967); N. W. Simmonds, Principles of Crop Improvement (Longman, London, 1979); J. Sneep et al., Plant Breeding Perspectives (Pudoc, Wageningen, 1979); and W. R. Fehr, Principles of Cultivar Development: Theory and Technique (Macmillan Pub., New York, N.Y., 1987).

Proper testing should detect any major faults and establish the level of superiority or improvement over current cultivars. In addition to showing superior performance, there must be a demand for a new cultivar or hybrid; i.e., the new cultivar or hybrid should either be compatible with industry standards, or it should create a new market. The introduction of a new cultivar or hybrid may incur additional costs to the seed producer, the grower, processor, and consumer for such things as special advertising and marketing, altered seed and commercial production practices, and new product utilization. The testing that precedes the release of a new cultivar or hybrid should take into account research and development costs, in addition to technical superiority of the final cultivar or hybrid.

In recent years, a few herbicide-tolerant rice varieties and hybrids have been successfully introduced to the market. See, e.g., U.S. Pat. Nos. 5,545,822; 5,736,629; 5,773,703; 5,773,704; 5,952,553; 6,274,796; 6,943,280; 7,019,196; 7,345,221; 7,399,905; 7,495,153; 7,754,947; and 7,786,360; published International Patent Applications WO 2010/059656, WO 2011/044315, and WO 2011/044334; and published U.S. patent applications US 2007/0061915, US 2010/0257623, US 2012/0204285, and US 2009/0025108. These herbicide-tolerant rice plants are resistant to or tolerant of herbicides that normally inhibit the growth of rice plants. Thus, rice growers now can control weeds that previously were difficult to control in rice fields, including "red rice." "Red rice" is a weedy relative of cultivated rice, and had previously been difficult to control because it actually belongs to the same genus (*Oryza*), and sometimes even the same species (*O. sativa*) as cultivated rice. Only recently, when herbicide tolerant rice became available, did it become possible to control red rice with herbicides in fields where cultivated rice was growing contemporaneously. There are currently only a limited number of herbicide-tolerant rice cultivars and hybrids available commercially. There is a continuing need for new herbicide-tolerant cultivars and hybrids—that is, rice plants that not only express a desired herbicide-tolerant phenotype, but that also possess other agronomically desirable characteristics. Additional herbicide-tolerant cultivars and hybrids will provide rice growers greater flexibility in planting and managing crops.

DISCLOSURE OF THE INVENTION

I have discovered a novel, herbicide-resistant, early maturing, semidwarf, medium-grain rice cultivar with improved yield and improved disease resistance, designated 'CL271.' This invention also pertains to methods for producing a hybrid or new variety by crossing the rice variety 'CL271' with another rice line, one or more times. Thus any such methods using the rice variety 'CL271' are aspects of this invention, including backcrossing, hybrid production, crosses to populations, and other breeding methods involving 'CL271.' Hybrid plants produced using the rice variety 'CL271' as a parent are also within the scope of this invention. Optionally, either parent can, through routine manipulation of cytoplasmic or other factors through techniques known in the art, be produced in a male-sterile form.

In another embodiment, this invention allows for single-gene converted plants of 'CL271.' The single transferred gene may be a dominant or recessive allele. Preferably, the single transferred gene confers a trait such as resistance to insects; resistance to one or more bacterial, fungal or viral diseases; male fertility or sterility; enhanced nutritional quality; enhanced processing qualities; or an additional source of herbicide resistance. The single gene may be a naturally occurring rice gene or a transgene introduced through genetic engineering techniques known in the art. The single gene also may be introduced through traditional backcrossing techniques or genetic transformation techniques known in the art.

In another embodiment, this invention provides regenerable cells for use in tissue culture of rice plant 'CL271.' The tissue culture may allow for regeneration of plants having physiological and morphological characteristics of rice plant 'CL271' and of regenerating plants having substantially the same genotype as rice plant 'CL271.' Tissue culture techniques for rice are known in the art. The regenerable cells in tissue culture may be derived from sources such as embryos, protoplasts, meristematic cells, callus, pollen, leaves, anthers, root tips, flowers, seeds, panicles, or stems. In addition, the invention provides rice plants regenerated from such tissue cultures.

In another embodiment, the present invention provides a method for controlling weeds in the vicinity of rice. The method comprises contacting the rice with a herbicide, wherein said rice belongs to any of (a) variety 'CL271' or (b) a hybrid, derivative, or progeny of 'CL271' that expresses the imidazolinone herbicide resistance characteristics of 'CL271.'

In some embodiments, the herbicide is an imidazolinone herbicide, a sulfonylurea herbicide, or a combination thereof.

In one embodiment, the rice is a rice plant and said contacting comprises applying the herbicide in the vicinity of the rice plant.

In another embodiment, the herbicide is applied to weeds in the vicinity of the rice plant.

In still further embodiments, the rice is a rice seed and said contacting comprises applying the herbicide to the rice seed.

In some embodiments, the present invention provides a method for treating rice. The method comprises contacting the rice with an agronomically acceptable composition, wherein said rice belongs to any of (a) variety 'CL271' or (b) a hybrid, derivative, or progeny of 'CL271' that expresses the imidazolinone herbicide resistance characteristics of 'CL271.'

In one embodiment, the agronomically acceptable composition comprises at least one agronomically acceptable active ingredient.

In another embodiment, the agronomically acceptable active ingredient is selected from the group consisting of fungicides, insecticides, antibiotics, stress tolerance-enhancing compounds, growth promoters, herbicides, molluscicides, rodenticides, and animal repellants, and combinations thereof.

In some embodiments, the rice plants of the present invention include plants that comprise an AHASL polypeptide (acetohydroxyacid synthase large subunit) having, relative to the wild-type AHASL polypeptide, an asparagine (N) at amino acid position 653 (*Arabidopsis thaliana* AHASL numbering) or equivalent position, wherein such a plant has increased tolerance to an imidazolinone herbicide when compared to a wild-type rice plant.

Amino acid position 653 of *Arabidopsis thaliana* AHASL corresponds to amino acid position 627 of *Oryza sativa* AHASL. In the wild-type rice AHASL polypeptide, this position is a Serine (S) in the conserved region Isoleucine-Proline-Serine-Glycine-Glycine (IPSGG) (SEQ ID NO:1).

In other embodiments, the rice plants of the present invention include plants that comprise an AHASL polypeptide having the amino acid sequence as set forth in SEQ ID NO:2 or a full-length, mature AHASL sequence variant thereof, wherein the variant comprises (i) the asparagine (N) at amino acid position 653 (*Arabidopsis thaliana* AHASL numbering) or equivalent position and (ii) one or more conservative substitutions at one or more non-essential amino acid residues.

In one embodiment, the full-length, mature AHASL sequence variant has, over the full-length of the variant, at least about 95%, illustratively, at least about: 95%, 96%, 97%, 98%, 99%, 99.5%, and 99.9% sequence identity to SEQ ID NO:2.

In some embodiments, the present invention provides a progeny rice line or variety obtainable from rice line 'CL271,' a representative sample of seeds of said line 'CL271' having been deposited under ATCC Accession No. PTA-120713, said line 'CL271' having been produced by a process comprising:
(a) providing a rice seed of the Cypress variety (USDA ARS GRIN NPGS Accession No. PI 561734); and
(b) mutagenizing said rice seed to produce an altered plant that contains in its genome an AHASL gene encoding an AHASL polypeptide having, relative to the wild-type AHASL polypeptide of the Cypress rice, an asparagine (N) substitution at amino acid position 653 (*Arabidopsis thaliana* AHASL numbering) or equivalent position, and further breeding the altered plant, wherein said altered plant of step (b) exhibits, upon expression of said AHASL gene, an increased tolerance to an imidazolinone herbicide as compared to that of plants of said Cypress variety, and plants of said line 'CL271' and plants of said progeny line or variety contain said AHASL gene and exhibit said increased tolerance.

In other embodiments, the present invention provides a progeny rice line or variety obtained from rice line 'CL271,' a representative sample of seeds of said line 'CL271' having been deposited under ATCC Accession No. PTA-120713, said line 'CL271' having been produced by a process comprising:
(a) providing a rice seed of the Cypress variety (USDA ARS GRIN NPGS Accession No. PI 561734); and
(b) mutagenizing said rice seed to produce an altered plant that contains in its genome an AHASL gene encoding an AHASL polypeptide having, relative to the wild-type AHASL polypeptide of the Cypress rice, an asparagine (N) substitution at amino acid position 653 (*Arabidopsis thaliana* AHASL numbering) or equivalent position, and further breeding the altered plant, wherein said altered plant of step (b) exhibits, upon expression of said AHASL gene, an increased tolerance to an imidazolinone herbicide as compared to that of plants of said Cypress variety, and plants of said line 'CL271' and plants of said progeny line or variety contain said AHASL gene and exhibit said increased tolerance.

In some embodiments, the present invention provides a progeny rice plant obtainable from rice line 'CL271,' a representative sample of seeds of said line 'CL271' having been deposited under ATCC Accession No. PTA-120713, said line 'CL271' having been produced by a process comprising:
(a) providing a rice seed of the Cypress variety (USDA ARS GRIN NPGS Accession No. PI 561734); and
(b) mutagenizing said rice seed to produce an altered plant that contains in its genome an AHASL gene encoding an AHASL polypeptide having, relative to the wild-type AHASL polypeptide of the Cypress rice, an asparagine (N) substitution at amino acid position 653 (*Arabidopsis thaliana* AHASL numbering) or equivalent position, and further breeding the altered plant, wherein said altered plant of step (b) exhibits, upon expression of said AHASL gene, an increased tolerance to an imidazolinone herbicide as compared to that of plants of said Cypress variety, and plants of said line 'CL271' and said progeny rice plant comprise said AHASL gene and exhibit said increased tolerance.

In some embodiments, the present invention provides a progeny rice plant obtained from rice line 'CL271,' a representative sample of seeds of said line 'CL271' having been deposited under ATCC Accession No. PTA-120713, said line 'CL271' having been produced by a process comprising:
(a) providing a rice seed of the Cypress variety (USDA ARS GRIN NPGS Accession No. PI 561734); and
(b) mutagenizing said rice seed to produce an altered plant that contains in its genome an AHASL gene encoding an AHASL polypeptide having, relative to the wild-type AHASL polypeptide of the Cypress rice, an asparagine (N) substitution at amino acid position 653 (*Arabidopsis thaliana* AHASL numbering) or equivalent position, and further breeding the altered plant, wherein said altered plant of step (b) exhibits, upon expression of said AHASL gene, an increased tolerance to an imidazolinone herbicide as compared to that of plants of said Cypress variety, and plants of said line 'CL271' and said progeny rice plant comprise said AHASL gene and exhibit said increased tolerance.

In another embodiment, the present invention provides a progeny rice plant of rice line 'CL271,' a representative sample of seeds of said line 'CL271' having been deposited under ATCC Accession No. PTA-120713, the progeny rice plant being obtainable by a process comprising:
(a) providing a plant of line 'CL271,' or tissue, seed, or cell thereof; and
(b) mutagenizing or transforming said plant, tissue, seed, or cell of step (a) to produce an altered plant that contains in its genome an AHASL gene encoding an AHASL polypeptide having, relative to the wild-type AHASL polypeptide of a wild-type rice plant, an asparagine (N) substitution at amino acid position 653 (*Arabidopsis thaliana* AHASL numbering) or equivalent position, and optionally further breeding the altered plant, wherein said altered plant of step (b) exhibits, upon expression of said AHASL gene, an increased tolerance to an imidazolinone herbicide as compared to that of the wild-type rice plant.

In another embodiment, the present invention provides a progeny rice plant of rice line 'CL271,' a representative sample of seeds of said line 'CL271' having been deposited under ATCC Accession No. PTA-120713, the progeny rice plant being obtained by a process comprising:
(a) providing a plant of line 'CL271,' or tissue, seed, or cell thereof; and (b) mutagenizing or transforming said plant, tissue, seed, or cell of step (a) to produce an altered plant that contains in its genome an AHASL gene encoding an AHASL polypeptide having, relative to the wild-type AHASL polypeptide of a wild-type rice plant, an asparagine (N) substitution at amino acid position 653 (*Arabidopsis thaliana* AHASL numbering) or equivalent position, and optionally further breeding the altered plant, wherein said altered plant of step (b) exhibits, upon expression of said AHASL gene, an increased tolerance to an imidazolinone herbicide as compared to that of the wild-type rice plant.

In other embodiments, the present invention provides a method for controlling weeds in a field, said method comprising:
  growing, in a field, a plant according to the present invention; and
  contacting said plant and weeds in the field with an effective amount of an AHAS-inhibiting herbicide to which the plant is tolerant, thereby controlling the weeds.

In some embodiments, improved rice plants and rice lines having tolerance to at least one AHAS-inhibitor herbicide are provided. In some embodiments, the AHAS-inhibitor herbicide is an imidazolinone herbicide. In some embodiments, the imidazolinone herbicide is imazethapyr, imazaquin, imazapyr, imazamox, or combinations thereof. Several examples of commercially available imidazolinone herbicides are, without limitation, PURSUIT® (imazethapyr), SCEPTER® (imazaquin), ARSENAL® (imazapyr), and Raptor™ Herbicide (imazamox). In some embodiments, the AHAS-inhibitor herbicide is a sulfonylurea herbicide. In one embodiment, the sulfonylurea herbicide is nicosulfuron.

The rice plants and rice lines of the present invention also provide for improved systems and methods for controlling weeds using at least one AHAS-inhibitor herbicide. In some embodiments, the AHAS-inhibitor herbicide is an imidazolinone herbicide. In some embodiments, the imidazolinone herbicide is imazethapyr, imazaquin, imazapyr, imazamox, or combinations thereof. In some embodiments, the AHAS-inhibitor herbicide is a sulfonylurea herbicide. In one embodiment, the sulfonylurea herbicide is nicosulfuron.

In some embodiments, the AHAS-inhibitor herbicide is an imidazolinone herbicide, a sulfonylurea herbicide, or combinations thereof.

DEFINITIONS

The following definitions apply throughout the specification and claims, unless context clearly indicates otherwise:

"Days to 50% heading." Average number of days from seeding to the day when 50% of all panicles are exerted at least partially through the leaf sheath. A measure of maturity.

"Grain Yield." Grain yield is measured in pounds per acre, at 12.0% moisture. Grain yield depends on a number of factors, including the number of panicles per unit area, the number of fertile florets per panicle, and grain weight per floret.

"Lodging Percent." Lodging is a subjectively measured rating, and is the percentage of plant stems leaning or fallen completely to the ground before harvest.

"Grain Length (L)." Length of a rice grain, or average length, measured in millimeters.

"Grain Width (W)." Width of a rice grain, or average width, measured in millimeters.

"Length/Width (L/W) Ratio." This ratio is determined by dividing the average length (L) by the average width (W).

"1000 Grain Wt." The weight of 1000 rice grains, measured in grams.

"Harvest Moisture." The percentage moisture in the grain when harvested.

"Plant Height." Plant height in centimeters, measured from soil surface to the tip of the extended panicle at harvest.

"Apparent Amylose Percent." The percentage of the endosperm starch of milled rice that is amylose. The apparent amylose percent is an important grain characteristic that affects cooking behavior. Standard long grains contain 20 to 23 percent amylose. Rexmont-type long grains contain 24 to 25 percent amylose. Short and medium grains contain 13 to 19 percent amylose. Waxy rice contains zero percent amylose. Amylose values, like most characteristics of rice, depend on the environment. "Apparent" refers to the procedure for determining amylose, which may also involve measuring some long chain amylopectin molecules that bind to some of the amylose molecules. These amylopectin molecules actually act similar to amylose in determining the relative hard or soft cooking characteristics.

"Alkali Spreading Value." An index that measures the extent of disintegration of the milled rice kernel when in contact with dilute alkali solution. It is an indicator of gelatinization temperature. Standard long grains have a 3 to 5 Alkali Spreading Value (intermediate gelatinization temperature).

"Peak Viscosity." The maximum viscosity attained during heating when a standardized, instrument-specific protocol is applied to a defined rice flour-water slurry.

"Trough Viscosity." The minimum viscosity after the peak, normally occurring when the sample starts to cool.

"Final Viscosity." Viscosity at the end of the test or cold paste.

"Breakdown." The peak viscosity minus the hot paste viscosity.

"Setback." Setback 1 is the final viscosity minus the trough viscosity. Setback 2 is the final viscosity minus the peak viscosity.

"RVA Viscosity." Viscosity, as measured by a Rapid Visco Analyzer, a widely used laboratory instrument to examine the paste viscosity or thickening ability of milled rice during the cooking process.

"Hot Paste Viscosity." Viscosity measure of rice flour/water slurry after being heated to 95° C. Lower values indicate softer and stickier cooking types of rice.

"Cool Paste Viscosity." Viscosity measure of rice flour/water slurry after being heated to 95° C. and uniformly cooled to 50° C. Values less than 200 indicate softer cooking types of rice.

"Allele." An allele is any of one or more alternate forms of the same gene. In a diploid cell or organism such as rice, the two alleles of a given gene occupy corresponding loci on a pair of homologous chromosomes.

"Backcrossing." Backcrossing is a process in which a breeder repeatedly crosses hybrid progeny back to one of the parents, for example, crossing a first generation hybrid $F_1$ with one of the parental genotypes of the $F_1$ hybrid, and then crossing a second generation hybrid $F_2$ with the same parental genotype, and so forth.

"Essentially all the physiological and morphological characteristics." A plant having "essentially all the physiological and morphological characteristics" of a specified plant refers to a plant having the same general physiological and morphological characteristics, except for those characteristics that are derived from a particular converted gene.

"Quantitative Trait Loci (QTL)." Quantitative trait loci (QTL) refer to genetic loci that to some degree control numerically measurable traits, generally traits that are continuously distributed.

"Regeneration." Regeneration refers to the development of a plant from tissue culture.

"Single Gene Converted (Conversion)." Single gene converted (conversion) includes plants developed by backcrossing wherein essentially all of the desired morphological and physiological characteristics of a parental variety are recovered, while also retaining a single gene that is transferred into the plants via crossing and backcrossing. The term can also refer to the introduction of a single gene through genetic engineering techniques known in the art.

MODES FOR CARRYING OUT THE INVENTION

'CL271' is a is a very high yielding, early maturing, semidwarf, medium-grain rice variety with improved yield and disease resistance. 'CL271' contains, by direct descent, the same allele for herbicide resistance as that found in the cultivar 'CL161.' The pedigree for this line is 'Neptune'//'Bengal'//'CL161.' 'CL161' is an imazethapyr-resistant mutant derived from the variety Cypress. See U.S. Pat. No. 7,019,196. 'CL271' is highly resistant to imidazolinone herbicides, including but not limited to imazethapyr and imazamox. The herbicide resistance characteristics of 'CL271' are essentially identical to the herbicide resistance characteristics of the variety 'CL161' (ATCC deposit PTA-904), also known as line PWC16 as disclosed by U.S. Pat. Nos. 6,943,280 and 7,019,196. Further, U.S. Pat. No. 6,943,280 discloses that in the AHAS enzyme DNA sequence of line PWC16, the codon corresponding to amino acid 627 is AAT, which encodes asparagine, versus AGT (serine) for the wild-type, and that this serine-to-asparagine substitution is believed to be responsible for the herbicide resistance displayed by the AHAS enzyme of line PWC16. 'CL271' and its hybrids and derived varieties are adapted for growing throughout the rice growing areas of Louisiana, Texas, Arkansas, Mississippi and Missouri; and will also be well suited for growing in many other rice-producing areas throughout the world.

'CL271' has a semidwarf stature, has excellent grain yield, good grain quality, and very good resistance to blast disease. 'CL271' was developed by a pedigree selection system at the Louisiana State University Rice Research Station in Crowley, La. The initial cross Neptune//Bengal//CL161 was made at the Rice Research Station (RRS). The line was developed from the bulk of a single F3 line (11P2512) made at the Puerto Rico winter nursery. Neptune is an early maturing medium-grain variety released by the Louisiana State University Rice Research Station in 2008. Bengal is an early maturing medium-grain rice variety released by the Louisiana State University Rice Research Station in 1992. CL161 is a Clearfield long-grain rice variety released from the Rice Research Station in 2002, and is essentially identical to ATCC deposit PTA-904. 'CL271' was evaluated in the Clearfield Preliminary Yield Trial at the Louisiana Rice Research Station with the experimental designation CLPR106 before being entered into the Cooperative Uniform Regional Rice Nurseries (URN) with the designation RUCL271.

| Generation | Test (Entry #) |
|---|---|
| F0 | 09CR 051 |
| F1 | 10T 051 |
| F2 | 10B 2035 |
| F3 | 11P 2512 |
| F4 | CLPR 106 |
| F5 | URN 065, CLPY 349 |
| F6 | Puerto Rico Headrows |
| F6 | URN 065, CA 208, CLR 006, CLPY 150, DP 011, PY 800 |
| F7 | Breeder Foundation Seed Production |

'CL271' averaged 38 inches in height in yield tests across Louisiana, which is the same height as CL261, and one inch taller than Caffey and Jupiter. At 90 days to 50% heading, it is three days later than CL261 and two days earlier than Caffey and Jupiter. The leaves, lemma, and palea of CL271 are glabrous. The spikelet and apiculus are straw-colored. The grain is non-aromatic.

'CL271' has a typical medium-grain cooking quality with low amylose content and low gelatinization temperature. The average amylose content of CL271 is 14.8%, compared with 15.0, 12.1 and 13.3% for CL261, Caffey and Jupiter, respectively. The average alkali spread value of CL271, CL261, Caffey and Jupiter are 6.0, 6.0, 5.8 and 6.0, respectively.

After the initial cross was made, the line was harvested and selected through early generations for phenotypic superiority for characteristics such as short plant architecture, grain shape and uniformity, seedling vigor, tiller number, and grain size. In later generations (seed increase), the line was selected for uniformity and purity both within and between panicle rows. Variants removed from seed-increase fields of 'CL271' were primarily taller or later plants. Other variants included any combination of the following: pubescent, taller, shorter, later, earlier, short-, long- and intermediate-grain types, gold and black hull, and sterile panicle. The overall incidence of variants less than 1 per 5,000 plants. Foundation seed rice was eventually grown beginning with the $F_7$ generation. Seed from the $F_5$, $F_6$, and $F_7$ generations were entered into an experimental line testing program, and were also tested at several locations in Louisiana rice producing areas. 'CL271' has been observed to be stable for at least three generations. 'CL271' is an inbred, stable, essentially homozygous line. 'CL271' is susceptible to bacterial panicle blight, moderately susceptible to rice sheath blight and straighthead, and is resistant to *Cercospora* and blast.

Variety Description Information

Rice cultivar 'CL271' was observed to possess the following morphological and other characteristics, based on averages of tests conducted at multiple during two growing seasons; data for varieties 'CL261,' 'Caffey,' and 'Jupiter' are shown for comparison:

TABLE 1

Average main crop yields (lb/A) for CL271, CL261, Caffey and Jupiter across several trials at multiple locations in Louisiana (Year 1-Year 2).

| YEAR | TEST | CL271 | CL261 | CAFFEY | JUPITER |
|---|---|---|---|---|---|
| Year1 | URN - LOUISIANA | 9463 | 2352 | 8704 | 8459 |
| | URN - ARKANSAS | 10189 | 8418 | 10283 | 11159 |
| | URN - MISSISSIPPI | 9853 | 8117 | 10375 | 10494 |
| | URN - TEXAS | 8126 | 7516 | 7679 | 9129 |
| | Year 1 Average | 9408 | 6601 | 9260 | 9810 |

TABLE 1-continued

Average main crop yields (lb/A) for CL271, CL261, Caffey and Jupiter across several trials at multiple locations in Louisiana (Year 1-Year 2).

| YEAR | TEST | CL271 | CL261 | CAFFEY | JUPITER |
|---|---|---|---|---|---|
| Year2 | CA - RRS | 8481 | 8247 | 7934 | 9440 |
|  | CA - ACADIA | 8893 | 8577 | 7878 | 8178 |
|  | CA - EVANGELINE | 8416 | 7761 | 7274 | 7360 |
|  | CA - FRANKLIN | 11242 | 9739 | 12150 | 10524 |
|  | CA - ST. LANDRY | 6633 | 5704 | 5387 | 7420 |
|  | PY - RRS | 8307 | 7184 | 3159 | 5962 |
|  | URN - RRS | 10050 | 10497 | 9881 | 8979 |
|  | Year 2 Average | 8860 | 8244 | 7666 | 8266 |
|  | Year 1-Year 2 Grand Average | 9059 | 7646 | 8246 | 8828 |

TABLE 2

Average main crop yields (lb/A) for CL271 and CL261 across several trials at multiple locations in Louisiana (Year 1-Year 2).

| YEAR | TEST | CL271 | CL261 |
|---|---|---|---|
| Year 1 | CLPY - RRS | 8169 | 2699 |
|  | URN - LOUISIANA | 9463 | 2352 |
|  | URN - ARKANSAS | 10189 | 8418 |
|  | URN - MISSISSIPPI | 9853 | 8117 |
|  | URN - TEXAS | 8126 | 7516 |
|  | Year 1 Average | 9160 | 5820 |
| Year 2 | CA - RRS | 8481 | 8247 |
|  | CA - ACADIA | 8893 | 8577 |
|  | CA - EVANGELINE | 8416 | 7761 |
|  | CA - FRANKLIN | 11242 | 9739 |
|  | CA - ST. LANDRY | 6633 | 5704 |
|  | CL MULTI - RRS | 9229 | 8683 |
|  | CL MULTI - EVANGELINE | 10028 | 8929 |
|  | CL MULTI - LAKE ARTHUR | 8491 | 8467 |
|  | CL MULTI - RICHLAND | 9139 | 8674 |
|  | CLPY - RRS | 9370 | 7753 |
|  | CLPY - LAKE ARTHUR | 7836 | 9051 |
|  | PY - RRS | 8307 | 7184 |
|  | URN - RRS | 10050 | 10497 |
|  | Year 2 Average | 8932 | 8405 |
|  | Year 1-Year 2 Grand Average | 8995 | 7687 |

TABLE 3

Whole rice yield (%) for CL271, CL261, Caffey and Jupiter across several trials at multiple locations in Louisiana (Year 1-Year 2).

| YEAR | TEST | CL271 | CL261 | CAFFEY | JUPITER |
|---|---|---|---|---|---|
| Year1 | URN - LOUISIANA | 64.2 | 54.2 | 58.5 | 57.1 |
|  | URN - ARKANSAS | 53.5 | 49.8 | 60.0 | 62.2 |
|  | URN - MISSISSIPPI | 53.0 | 48.4 | 54.1 | 59.6 |
|  | URN - TEXAS | 56.4 | 58.6 | 55.3 | 62.0 |
|  | Year 1 Average | 56.8 | 52.8 | 57.0 | 60.2 |
| Year2 | CA - RRS | 60.7 | 64.2 | 57.4 | 56.4 |
|  | CA - ACADIA | 60.9 | 61.6 | 60.0 | 59.3 |
|  | PY - RRS | 71.6 | 67.7 | 66.7 | 67.0 |
|  | URN - RRS | 63.3 | 65.5 | 59.0 | 58.4 |
|  | Year 2 Average | 64.1 | 64.8 | 60.8 | 60.8 |
|  | Year 1-Year 2 Grand Average | 60.1 | 58.8 | 58.9 | 60.3 |

TABLE 4

Whole rice yield (%) for CL271 and CL261 across several trials at multiple locations in Louisiana (Year 1-Year 2).

| YEAR | TEST | CL271 | CL261 |
|---|---|---|---|
| Year1 | URN - LOUISIANA | 64.2 | 54.2 |
|  | URN - ARKANSAS | 53.5 | 49.8 |
|  | URN - MISSISSIPPI | 53.0 | 48.4 |
|  | URN - TEXAS | 56.4 | 58.6 |
|  | CLPY - RRS | 63.2 | 53.2 |
|  | Year 1 Average | 58.0 | 52.8 |
| Year2 | CA - RRS | 60.7 | 64.2 |
|  | CA - ACADIA | 60.9 | 61.6 |
|  | CL MULTI - RRS | 62.1 | 63.4 |
|  | CLPY - RRS | 63.3 | 65.8 |
|  | PY - RRS | 71.6 | 67.7 |
|  | URN - RRS | 63.3 | 65.5 |
|  | Year 2 Average | 63.7 | 64.7 |
|  | Year 1-Year 2 Grand Average | 61.1 | 59.3 |

TABLE 5

Total rice yield (%) for CL271, CL261, Caffey and Jupiter across several trials at multiple locations in Louisiana (Year 1-Year 2).

| YEAR | TEST | CL271 | CL261 | CAFFEY | JUPITER |
|---|---|---|---|---|---|
| Year1 | URN - LOUISIANA | 69.8 | 63.3 | 67.1 | 65.6 |
|  | URN - ARKANSAS | 69.0 | 69.2 | 69.1 | 68.1 |
|  | URN - MISSISSIPPI | 67.6 | 64.4 | 66.4 | 66.1 |
|  | URN - TEXAS | 68.5 | 69.0 | 68.2 | 66.3 |
|  | Year 1 Average | 68.7 | 66.5 | 67.7 | 66.5 |
| Year2 | CA - RRS | 69.8 | 68.6 | 64.5 | 63.2 |
|  | CA - ACADIA | 70.1 | 69.2 | 68.0 | 66.5 |
|  | PY - RRS | 74.4 | 73.0 | 73.9 | 71.7 |
|  | URN - RRS | 68.3 | 69.9 | 66.0 | 65.0 |
|  | Year 2 Average | 70.7 | 70.2 | 68.1 | 66.6 |
|  | Year 1-Year 2 Grand Average | 69.7 | 68.3 | 67.9 | 66.6 |

TABLE 6

Total rice yield (%) for CL271 and CL261 across several trials at multiple locations in Louisiana (Year 1-Year 2).

| YEAR | TEST | CL271 | CL261 |
|---|---|---|---|
| Year1 | URN - LOUISIANA | 69.8 | 63.3 |
|  | URN - ARKANSAS | 69.0 | 69.2 |
|  | URN - MISSISSIPPI | 67.6 | 64.4 |
|  | URN - TEXAS | 68.5 | 69.0 |
|  | CLPY - RRS | 68.2 | 62.3 |
|  | Year 1 Average | 68.6 | 65.6 |
| Year2 | CA - RRS | 69.8 | 68.6 |
|  | CA - ACADIA | 70.1 | 69.2 |
|  | CL MULTI - RRS | 69.3 | 68.6 |
|  | CLPY - RRS | 68.4 | 70.2 |
|  | PY - RRS | 74.4 | 73.0 |
|  | URN - RRS | 68.3 | 69.9 |
|  | Year 2 Average | 70.1 | 69.9 |
|  | Year 1-Year 2 Grand Average | 68.3 | 67.0 |

TABLE 7

Seedling vigor for CL271, CL261, Caffey and Jupiter across several trials at multiple locations in Louisiana (Year 1-Year 2).

| YEAR | TEST | CL271 | CL261 | CAFFEY | JUPITER |
|---|---|---|---|---|---|
| Year1 | URN - LOUISIANA | 4 | 4 | 4 | 5 |
|  | Year 1 | 4 | 4 | 4 | 5 |
| Year2 | CA - RRS | 6 | 4 | 5 | 5 |
|  | CA - ACADIA | 5 | 4 | 5 | 5 |
|  | PY - RRS | 5 | 5 | 5 | 5 |
|  | URN - RRS | 5 | 4 | 4 | 5 |
|  | Year 2 Average | 5 | 4 | 5 | 5 |
|  | Year 1-Year 2 Grand Average | 5 | 4 | 5 | 5 |

TABLE 8

Seedling vigor for CL271 and CL261 across several trials at multiple locations in Louisiana (Year 1-Year 2).

| YEAR | TEST | CL271 | CL261 |
|---|---|---|---|
| Year1 | URN - LOUISIANA | 4 | 4 |
|  | CLPY - RRS | 4 | 4 |
|  | Year 1 Average | 4 | 4 |
| Year2 | CA - RRS | 6 | 4 |
|  | CA - ACADIA | 5 | 4 |
|  | CL MULTI - RRS | 4 | 4 |
|  | CLPY - RRS | 4 | 5 |
|  | PY - RRS | 5 | 5 |
|  | URN - RRS | 5 | 4 |
|  | Year 2 Average | 5 | 4 |
|  | Year 1-Year 2 Grand Average | 5 | 4 |

TABLE 9

Mean plant height (in) for CL271, CL261, Caffey and Jupiter across several trials at multiple locations in Louisiana (Year 1-Year 2).

| YEAR | TEST | CL271 | CL261 | CAFFEY | JUPITER |
|---|---|---|---|---|---|
| Year1 | URN - LOUISIANA | 36 | 35 | 36 | 37 |
|  | URN - ARKANSAS | 37 | 37 | 39 | 36 |
|  | URN - TEXAS | 39 | 39 | 39 | 37 |
|  | Year 1 Average | 37 | 37 | 38 | 37 |
| Year2 | CA - RRS | 37 | 39 | 36 | 36 |
|  | CA - ACADIA | 37 | 37 | 34 | 31 |
|  | CA - EVANGELINE | 38 | 37 | 38 | 34 |
|  | CA - FRANKLIN | 47 | 46 | 44 | 42 |
|  | CA - ST. LANDRY | 35 | 35 | 33 | 38 |
|  | PY - RRS | 33 | 34 | 31 | 34 |
|  | URN - RRS | 36 | 36 | 38 | 38 |
|  | Year 2 Average | 38 | 38 | 36 | 36 |
|  | Year 1-Year 2 Grand Average | 38 | 38 | 37 | 37 |

TABLE 10

Mean plant height (in) for CL271 and CL261 across several trials at multiple locations in Louisiana (Year 1-Year 2).

| YEAR | TEST | CL271 | CL261 |
|---|---|---|---|
| Year 1 | CLPY - RRS | 37 | 38 |
|  | URN - LOUISIANA | 36 | 35 |
|  | URN - ARKANSAS | 37 | 37 |
|  | URN - TEXAS | 39 | 39 |
|  | Year 1 Average | 37 | 37 |
| Year 2 | CA - RRS | 37 | 39 |
|  | CA - ACADIA | 37 | 37 |
|  | CA - EVANGELINE | 38 | 37 |
|  | CA - FRANKLIN | 47 | 46 |
|  | CA - ST. LANDRY | 35 | 35 |
|  | CL MULTI - RRS | 37 | 39 |
|  | CL MULTI - EVANGELINE | 39 | 39 |
|  | CL MULTI - LAKE ARTHUR | 39 | 40 |
|  | CL MULTI - RICHLAND | 40 | 39 |
|  | CLPY - RRS | 34 | 36 |
|  | PY - RRS | 33 | 34 |
|  | URN - RRS | 36 | 36 |
|  | Year 2 Average | 38 | 38 |
|  | Year 1-Year 2 Grand Average | 38 | 38 |

TABLE 11

Mean number of days to 50% heading for CL271, CL261, Caffey and Jupiter across several trials at multiple Louisiana locations (Year 1-Year 2).

| YEAR | TEST | CL271 | CL261 | CAFFEY | JUPITER |
|---|---|---|---|---|---|
| Year1 | URN - LOUISIANA | 85 | 81 | 84 | 88 |
|  | URN - ARKANSAS | 94 | 94 | 95 | 96 |
|  | URN - MISSISSIPPI | 81 | 74 | 79 | 80 |
|  | URN - TEXAS | 88 | 85 | 87 | 93 |
|  | Year 1 Average | 87 | 83 | 86 | 89 |
| Year2 | CA - RRS | 91 | 88 | 92 | 92 |
|  | CA - ACADIA | 92 | 90 | 96 | 97 |
|  | CA - EVANGELINE | 90 | 85 | 96 | 92 |
|  | CA - FRANKLIN | 73 | 68 | 72 | 73 |
|  | CA - ST. LANDRY | 100 | 94 | 99 | 101 |
|  | PY - RRS | 91 | 90 | 99 | 99 |
|  | URN - RRS | 90 | 91 | 91 | 93 |
|  | Year 2 Average | 90 | 87 | 92 | 92 |
|  | Year 1-Year 2 Grand Average | 89 | 85 | 90 | 91 |

TABLE 12

Mean number of days to 50% heading for CL271, CL261, across several trials at multiple locations in Louisiana (Year 1-Year 2).

| YEAR | TEST | CL271 | CL261 |
|---|---|---|---|
| Year 1 | CLPY - RRS | 85 | 85 |
|  | URN - LOUISIANA | 85 | 81 |
|  | URN - ARKANSAS | 94 | 94 |
|  | URN - MISSISSIPPI | 81 | 74 |
|  | URN - TEXAS | 88 | 85 |
|  | Year 1 Average | 87 | 84 |
| Year 2 | CA - RRS | 91 | 88 |
|  | CA - ACADIA | 92 | 90 |
|  | CA - EVANGELINE | 90 | 85 |
|  | CA - FRANKLIN | 73 | 68 |
|  | CA - ST. LANDRY | 100 | 94 |
|  | CL MULTI - RRS | 90 | 89 |
|  | CL MULTI - EVANGELINE | 88 | 86 |
|  | CL MULTI - LAKE ARTHUR | 100 | 95 |
|  | CL MULTI - RICHLAND | 74 | 70 |
|  | CLPY - RRS | 93 | 92 |
|  | CLPY - LAKE ARTHUR | 97 | 94 |

TABLE 12-continued

Mean number of days to 50% heading for CL271, CL261, across several trials at multiple locations in Louisiana (Year 1-Year 2).

| YEAR | TEST | CL271 | CL261 |
|---|---|---|---|
| | PY - RRS | 91 | 90 |
| | URN - RRS | 80 | 91 |
| | Year 2 Average | 90 | 87 |
| | Year 1-Year 2 Grand Average | 89 | 86 |

TABLE 13

Reaction of CL271, CL261, Caffey and Jupiter to sheath blight (*Rhizoctonia solani*) (Year 2).

| YEAR | TEST | CL271 | CL261 | CAFFEY | JUPITER |
|---|---|---|---|---|---|
| Year 2 | VARIETY TRIAL | 5.4 | 6.4 | 5.4 | 5.2 |

* Using a scale of 0 = very resistant to 9 = very susceptible.

TABLE 14

Reaction of CL271, CL261, Caffey and Jupiter to blast (*Pyricularia oryzae*) (Year 1-Year 2).

| YEAR | TEST | CL271 | CL261 | CAFFEY | JUPITER |
|---|---|---|---|---|---|
| Year 1 | URN - RRS | 0.5 | 8.5 | 1.5 | 0.5 |
| Year 2 | VARIETY TRIAL | 1 | 5.4 | 3.4 | 0.6 |
| | Grand Average | 0.75 | 6.9 | 2.4 | 0.55 |

* Using a scale of 0 = very resistant to 9 = very susceptible.

TABLE 15

Reaction of CL271, CL261, Caffey and Jupiter to Cercospora (*Cercospora janseana*) (Year 2).

| YEAR | TEST | CL271 | CL261 | CAFFEY | JUPITER |
|---|---|---|---|---|---|
| Year 2 | VARIETY TRIAL | 0.6 | 0.4 | 0 | 0.2 |

* Using a scale of 0 = very resistant to 9 = very susceptible.

TABLE 16

Reaction of CL271, CL261, Caffey and Jupiter to bacterial panicle blight (*Xanthomonas oryzae*) (Year 2).

| YEAR | TEST | CL271 | CL261 | CAFFEY | JUPITER |
|---|---|---|---|---|---|
| Year 2 | VARIETY TRIAL | 6.2 | 7.4 | 4.6 | 4.8 |

* Using a scale of 0 = very resistant to 9 = very susceptible.

TABLE 17

Reaction of CL271, CL261, Caffey and Jupiter to the physiological disorder straighthead (Year 1-Year 2).

| YEAR | TEST | CL271 | CL261 | CAFFEY | JUPITER |
|---|---|---|---|---|---|
| Year 1 | RRS | 4.5 | 5.3 | 2.8 | 3.3 |
| Year 2 | RRS | 4.8 | 4.8 | 3.7 | 3.5 |
| | Grand Average | 4.7 | 5.1 | 3.3 | 3.4 |

TABLE 18

Rough, brown and milled grain dimensions and weight of CL271, CL261, Caffey and Jupiter grown in Crowley, LA.

| Variety | Type | Length mm | Width mm | L/W Ratio | Thickness | Weight |
|---|---|---|---|---|---|---|
| CL271 | Rough | 8.38 | 3.13 | 2.68 | 2.33 | 26.67 |
| | Brown | 6.26 | 2.68 | 2.34 | 1.92 | 22.20 |
| | Milled | 6.06 | 2.65 | 2.29 | 1.87 | 20.00 |
| CL261 | Rough | 8.08 | 2.93 | 2.76 | 1.99 | 24.62 |
| | Brown | 6.05 | 2.59 | 2.34 | 1.77 | 20.13 |
| | Milled | 5.75 | 2.51 | 2.29 | 1.70 | 16.91 |
| CAFFEY | Rough | 8.31 | 3.30 | 2.52 | 2.32 | 28.34 |
| | Brown | 6.07 | 2.74 | 2.22 | 1.98 | 23.09 |
| | Milled | 5.79 | 2.71 | 2.14 | 1.92 | 21.76 |
| JUPITER | Rough | 8.32 | 3.15 | 2.64 | 2.20 | 25.32 |
| | Brown | 6.07 | 2.66 | 2.28 | 1.97 | 22.67 |
| | Milled | 5.75 | 2.64 | 2.18 | 1.89 | 20.30 |

The variety is resistant to imidazolinone herbicides. The herbicide resistance profile is essentially the same as that of 'CL161' by direct descent. The herbicide tolerance allows 'CL271,' its hybrids, and derived varieties to be used with Clearfield™ rice technology and herbicides, including among others imazethapyr and imazamox, for the selective control of weeds, including red rice. See generally U.S. Pat. No. 6,943,280.

Herbicide tolerance and susceptibility characteristics:
The variety is tolerant to some herbicides, and susceptible to some herbicides, that normally inhibit the growth of rice plants. Among others, the herbicide tolerance and susceptibility characteristics of 'CL271' include or are expected to include the following. These characteristics are in some cases based on actual observations to date, and in other cases reflect assumptions based on direct descent from 'CL161':

'CL271' expresses a mutant acetohydroxyacid synthase whose enzymatic activity is directly resistant to normally-inhibitory levels of a herbicidally-effective imidazolinone;

'CL271' is resistant to each of the following imidazolinone herbicides, at levels of the imidazolinone herbicides that would normally inhibit the growth of a rice plant: imazethapyr, imazapic, imazaquin, imazamox, and imazapyr;

'CL271' is resistant to each of the following sulfonylurea herbicides, at levels of the sulfonylurea herbicides that would normally inhibit the growth of a rice plant: nicosulfuron, metsulfuron methyl, thifensulfuron methyl, and tribenuron methyl;

'CL271' is sensitive to each of the following sulfonylurea herbicides, at levels of the sulfonylurea herbicides that would normally inhibit the growth of a rice plant: sulfometuron methyl, chlorimuron ethyl, and rimsulfuron.

This invention is also directed to methods for producing a rice plant by crossing a first parent rice plant with a second parent rice plant, wherein the first or second rice plant is a rice plant from the line 'CL271.' Further, both first and second parent rice plants may be from the cultivar 'CL271,' although it is preferred that one of the parents should be different. Methods that use the cultivar 'CL271' are also part of this invention, including crossing, selfing, backcrossing, hybrid breeding, crossing to populations, the other breeding methods discussed in this specification, and other breeding methods known to those of skill in the art. Any plants produced using cultivar 'CL271' as a parent or ancestor are within the scope of this invention. The other parents or other lines used in such breeding programs may be any of the wide number of rice varieties, cultivars, populations, experimental lines, and other sources of rice germplasm known in the art.

For example, this invention includes methods for producing a first-generation hybrid rice plant by crossing a first parent rice plant with a second parent rice plant, wherein either the first or second parent rice plant is 'CL271.' Further, this invention is also directed to methods for producing a hybrid rice line derived from 'CL271' by crossing 'CL271' with a second rice plant, and growing the progeny seed. The crossing and growing steps may be repeated any number of times. Breeding methods using the rice line 'CL271' are considered part of this invention, not only backcrossing and hybrid production, but also selfing, crosses to populations, and other breeding methods known in the art.

Optionally, either of the parents in such a cross, 'CL271' or the other parent, may be produced in male-sterile form, using techniques known in the art.

In one embodiment, a rice plant produced using cultivar 'CL271' as a parent or ancestor exhibits tolerance to applications of one or more classes of herbicides. Classes of herbicides include, but are not limited to, acetohydroxyacid synthase (AHAS) inhibitors; bleaching herbicides such as hydroxyphenylpyruvate dioxygenase (HPPD) inhibitors or phytoene desaturase (PDS) inhibitors; enolpyruvyl shikimate 3-phosphate synthase (EPSPS) inhibitors such as glyphosate; glutamine synthetase (GS) inhibitors such as glufosinate; auxinic herbicides, e.g., dicamba; lipid biosynthesis inhibitors such as ACCase inhibitors; or oxynil (i.e. bromoxynil or ioxynil) herbicides; protoporphyrinogen-IX oxidase (PPO) inhibitors other than saflufenacil ("other PPO inhibitors") (e.g., acifluorfen, butafenacil, carfentrazone, flufenpyr-ethyl, fomesafen, flumiclorac, flumioxazin, lactofen, oxadiargyl, oxadiazon, oxyfluorfen, sulfentrazone); lipid biosynthesis inhibitors such as acetyl CoA carboxylase (ACCase) inhibitors; oxynil (i.e. bromoxynil or ioxynil) herbicides; ACCase-inhibitor(s); saflufenacil(s); p-hydroxyphenylpyruvate dioxygenase (4-HPPD) inhibitors; amide(s), e.g., propanil; and the like. AHAS-inhibitor herbicides include, e.g., imidazolinone herbicides, one or more sulfonylurea (SU) herbicides selected from the group consisting of amidosulfuron, flupyrsulfuron, foramsulfuron, imazosulfuron, iodosulfuron, mesosulfuron, nicosulfuron, thifensulfuron, and tribenuron, agronomically acceptable salts and esters thereof, and combinations thereof. ACCase inhibitor herbicides include, e.g., "dims" (e.g., cycloxydim, sethoxydim, clethodim, or tepraloxydim), "fops" (e.g., clodinafop, diclofop, fluazifop, haloxyfop, or quizalofop), and "dens" (such as pinoxaden).

For example, in some embodiments rice plants that are produced using cultivar 'CL271' as a parent or ancestor may be tolerant to ACCase inhibitors, such as "dims" (e.g., cycloxydim, sethoxydim, clethodim, or tepraloxydim), "fops" (e.g., clodinafop, diclofop, fluazifop, haloxyfop, or quizalofop), and "dens" (such as pinoxaden); to auxinic herbicides, such as dicamba; to EPSPS inhibitors, such as glyphosate; to other PPO inhibitors; and to GS inhibitors, such as glufosinate.

In addition to these classes of inhibitors, rice plants that are produced using cultivar 'CL271' as a parent or ancestor may also be tolerant to herbicides having other modes of action, for example, chlorophyll/carotenoid pigment inhibitors, cell membrane disruptors, photosynthesis inhibitors, cell division inhibitors, root inhibitors, shoot inhibitors, and combinations thereof.

Such tolerance traits may be expressed, e.g., as mutant acetohydroxyacid synthase large subunit (AHASL) proteins, mutant ACCase proteins, mutant EPSPS proteins, or mutant glutamine synthetase proteins; or as a mutant native, inbred, or transgenic aryloxyalkanoate dioxygenase (AAD or DHT), haloarylnitrilase (BXN), 2,2-dichloropropionic acid dehalogenase (DEH), glyphosate-N-acetyltransferase (GAT), glyphosate decarboxylase (GDC), glyphosate oxidoreductase (GOX), glutathione-S-transferase (GST), phosphinothricin acetyltransferase (PAT or bar), or cytochrome P450 (CYP450) protein having herbicide-degrading activity.

The rice plants hereof can also be "stacked" with other traits including, but not limited to, pesticidal traits such as Bt Cry and other proteins having pesticidal activity toward coleopteran, lepidopteran, nematode, or other pests; nutritional or nutraceutical traits such as modified oil content or oil profile traits, high protein or high amino acid concentration traits, and other trait types known in the art.

Furthermore, in another embodiment, rice plants are generated, e.g. by the use of recombinant DNA techniques, breeding, or otherwise by selection for desired traits, that are able to synthesize one or more proteins to improve their productivity, oil content, tolerance to drought, salinity or other growth-limiting environmental factors, or tolerance to arthropod pests, and fungal, bacterial, or viral pathogens of rice plants.

Furthermore, in other embodiments, rice plants are generated, e.g. by the use of recombinant DNA techniques, breeding, or otherwise by selection for desired traits to contain a modified amount of one or more substances or to contain one or more new substances, for example, to improve human or animal nutrition, e.g. health-promoting long-chain omega-3 fatty acids or unsaturated omega-9 fatty acids. (Cf. Nexera® canola, Dow Agro Sciences, Canada).

Furthermore, in some embodiments, rice plants are generated, e.g. by the use of recombinant DNA techniques, breeding, or otherwise by selection for desired traits to contain increased amounts of vitamins, minerals, or improved profiles of nutraceutical compounds.

In one embodiment, rice plants are produced using cultivar 'CL271' as a parent or ancestor so that the new rice plants, relative to a wild-type rice plant, comprise an increased amount of, or an improved profile of, a compound selected from the group consisting of: glucosinolates (e.g., glucoraphanin (4-methylsulfinylbutyl-glucosinolate), sulforaphane, 3-indolylmethyl-glucosinolate (glucobrassicin), or 1-methoxy-3-indolylmethyl-glucosinolate (neoglucobrassicin)); phenolics (e.g., flavonoids (e.g., quercetin, kaempferol), hydroxycinnamoyl derivatives (e.g., 1,2,2'-trisinapoylgentiobiose, 1,2-diferuloylgentiobiose, 1,2'-disinapoyl-2-feruloylgentiobiose, or 3-O-caffeoyl-quinic (neochlorogenic acid)); and vitamins and minerals (e.g., vitamin C, vitamin E, carotene, folic acid, niacin, riboflavin, thiamine, calcium, iron, magnesium, potassium, selenium, and zinc).

In another embodiment, rice plants are produced using cultivar 'CL271' as a parent or ancestor so that the new rice plants, relative to a wild-type rice plant, comprise an increased amount of, or an improved profile of, a compound selected from the group consisting of: progoitrin; isothiocyanates; indoles (products of glucosinolate hydrolysis); glutathione; carotenoids such as beta-carotene, lycopene, and the xanthophyll carotenoids such as lutein and zeaxanthin; phenolics comprising the flavonoids such as the flavonols (e.g. quercetin, rutin), the flavins/tannins (such as the procyanidins comprising coumarin, proanthocyanidins, catechins, and anthocyanins); flavones; phytoestrogens such as coumestans; lignans; resveratrol; isoflavones e.g. genistein, daidzein, and glycitein; resorcyclic acid lactones; organosulfur compounds; phytosterols; terpenoids such as carnosol, rosmarinic acid, glycyrrhizin and saponins; chlorophyll; chlorphyllin, sugars, anthocyanins, and vanilla.

Herbicides

Herbicidal compositions that may be used in conjunction with the invention include herbicidally active ingredients (A.I.), and their agronomically acceptable salts and esters.

The herbicidal compositions can be applied in any agronomically acceptable format. For example, they can be formulated as ready-to-spray aqueous solutions, powders, or suspensions; as concentrated or highly concentrated aqueous, oily or other solutions, suspensions or dispersions; as emulsions, oil dispersions, pastes, dusts, granules, or other broadcastable formats. The herbicidal compositions can be applied by any method known in the art, including, for example, spraying, atomizing, dusting, spreading, watering, seed treatment, or co-planting in admixture with the seed. The formulations depend on the intended purpose; in any case, they should ensure a fine distribution of the A.I.s. A herbicidal composition can be selected according to the tolerances of a particular plant, and the plant can be selected from among those having stacked tolerance traits.

In some embodiments, where the A.I. includes an AHAS inhibitor, the AHAS inhibitor may be selected from: (1) the imidazolinones, e.g. imazamox, imazethapyr, imazapyr, imazapic, imazaquin, and imazamethabenz; preferably imazamox, imazethapyr, imazapyr, or imazapic; (2) the sulfonylureas, e.g. amidosulfuron, azimsulfuron, bensulfuron, cinosulfuron, ethoxysulfuron, flupyrsulfuron, foramsulfuron, imazosulfuron, iodosulfuron, mesosulfuron, metsulfuron, nicosulfuron, thifensulfuron, and tribenuron; (3) the pyrimidinyloxy[thio]benzoates, e.g. including the pyrimidinyloxybenzoates (e.g., bispyribac, pyriminobac, and pyribenzoxim) and the pyrimidinylthiobenzoates (e.g., pyrithiobac and pyriftalid); and (4) the sulfonamides, e.g. including the sulfonylaminocarbonyltriazolinones (e.g., flucarbazone and propoxycarbazone) and the triazolopyrimidines (e.g., cloransulam, diclosulam, florasulam, flumetsulam, metosulam, and penoxsulam). The agronomically acceptable salts and esters of the foregoing are also included, as are combinations thereof.

Optional A.I.s of other types include, but are not limited to agronomically-acceptable fungicides such as strobilurins, e.g., pyraclostrobin, alone or in combination with, e.g., boscalid, epiconazole, metaconazole, tebuconazole, kresoxim-methyl, and the like; insecticides such as nematicides, lepidoptericides, coleoptericides; molluscicides), and others known in the art (e.g., malathion, pyrethrins/pyrethrum, carbaryl, spinosad, permethrin, bifenthrin, and esfenvalerate).

Examples of herbicides that are ACCase inhibitors include, but are not limited to, cyclohexanedione herbicides (DIMs, also referred to as: cyclohexene oxime cyclohexanedione oxime; and CHD), aryloxyphenoxy propionate herbicides (also referred to as aryloxyphenoxy propanoate; aryloxyphenoxyalkanoate; oxyphenoxy; APP; AOPP; APA; APPA; FOP), and phenylpyrazole herbicides (also known as DENs; and sometimes referred to under the more general class of phenylpyrazoles such as pinoxaden (e.g., herbicides sold under the trade names Axial and Traxos)). In some methods of controlling weeds or growing herbicide-tolerant plants, at least one herbicide is selected from the group consisting of sethoxydim, cycloxydim, tepraloxydim, haloxyfop, haloxyfop-P or a derivative of one of these herbicides. Table 19 lists examples of herbicides that interfere with ACCase activity.

TABLE 19

Examples of ACCase inhibitors.

| ACCase Inhibitor | Class | Company | Examples of Synonyms and Trade Names |
|---|---|---|---|
| alloxydim | DIM | BASF | Fervin, Kusagard, NP-48Na, BAS 9021H, Carbodimedon, Zizalon |
| butroxydim | DIM | Syngenta | Falcon, ICI-A0500, Butroxydim |
| clethodim | DIM | Valent | Select, Prism, Centurion, RE-45601, Motsa |
| Clodinafop-propargyl | FOP | Syngenta | Discover, Topik, CGA 184 927 |
| clofop | FOP | | Fenofibric Acid, Alopex |
| cloproxydim | FOP | | |
| chlorazifop | FOP | | |
| cycloxydim | DIM | BASF | Focus, Laser, Stratos, BAS 517H |
| cyhalofop-butyl | FOP | Dow | Clincher, XDE 537, DEH 112, Barnstorm |
| diclofop-methyl | FOP | Bayer | Hoegrass, Hoelon, Illoxan, HOE 23408, Dichlorfop, Illoxan |
| fenoxaprop-P-ethyl | FOP | Bayer | Super Whip, Option Super, Exel Super, HOE-46360, Aclaim, Puma S, Fusion |
| fenthiaprop | FOP | | Taifun; Joker |
| fluazifop-P-butyl | FOP | Syngenta | Fusilade, Fusilade 2000, Fusilade DX, ICI-A 0009, ICI-A 0005, SL-236, IH-773B, TF-1169, Fusion |
| haloxyfop-etotyl | FOP | Dow | Gallant, DOWCO 453EE |
| haloxyfop-methyl | FOP | Dow | Verdict, DOWCO 453ME |
| haloxyfop-P-methyl | FOP | Dow | Edge, DE 535 |
| isoxapyrifop | FOP | | |
| Metamifop | FOP | Dongbu | NA |
| pinoxaden | DEN | Syngenta | Axial |
| profoxydim | DIM | BASF | Aura, Tetris, BAS 625H, Clefoxydim |
| propaquizafop | FOP | Syngenta | Agil, Shogun, Ro 17-3664, Correct |
| quizalofop-P-ethyl | FOP | DuPont | Assure, Assure II, DPX-Y6202-3, Targa Super, NC-302, Quizafop |
| quizalofop-P-tefuryl | FOP | Uniroyal | Pantera, UBI C4874 |
| sethoxydim | DIM | BASF | Poast, Poast Plus, NABU, Fervinal, NP-55, Sertin, BAS 562H, Cyethoxydim, Rezult |
| tepraloxydim | DIM | BASF | BAS 620H, Aramo, Caloxydim |
| tralkoxydim | DIM | Syngenta | Achieve, Splendor, ICI-A0604, Tralkoxydime, Tralkoxidym |
| trifop | FOP | | |

Examples of herbicides that are auxinic herbicides include, but are not limited to, those shown in Table 20.

TABLE 20

Examples of Auxinic herbicides.
Classification of Auxinic Herbicides
(HRAC Group 'O'; WSSA Group '4')

| Subgroup | Member Compound |
|---|---|
| Phenoxy-carboxylic-acid Subgroup | Clomeprop<br>cloprop ("3-CPA")<br>4-chlorophenoxyacetic acid ("4-CPA")<br>2-(4-chlorophenoxy)propionic acid ("4-CPP")<br>2,4-dichlorophenoxy acetic acid ("2,4-D")<br>(3,4-dichlorophenoxy)acetic acid ("3,4-DA")<br>4-(2,4-dichlorophenoxy)butyric acid ("2,4-DB")<br>2-(3,4-dichlorophenoxy)propionic acid ("3,4-DP")<br>tris[2-(2,4-dichlorophenoxy)ethyl]phosphite ("2,4-DEP")<br>dichlorprop ("2,4-DP")<br>2,4,5-trichlorophenoxyacetic acid ("2,4,5-T")<br>fenoprop ("2,4,5-TP")<br>2-(4-chloro-2-methylphenoxy)acetic acid ("MCPA")<br>4-(4-chloro-2-methylphenoxy)butyric acid ("MCPB")<br>mecoprop ("MCPP") |

TABLE 20-continued

Examples of Auxinic herbicides.
Classification of Auxinic Herbicides
(HRAC Group 'O'; WSSA Group '4')

| Subgroup | Member Compound |
| --- | --- |
| Benzoic acid Subgroup | Chloramben |
| | Dicamba |
| | Tricamba |
| | 2,3,6-trichlorobenzoic acid ("TBA") |
| Pyridine carboxylic acid Subgroup | Aminopyralid |
| | Clopyralid |
| | Fluroxypyr |
| | Picloram |
| | Triclopyr |
| Quinoline carboxylic acid Subgroup | Quinclorac |
| | Quinmerac |
| Other Subgroup | Benazolin |

In one embodiment, a saflufenacil A.I. is, e.g.: 2-chloro-5-[3,6-dihydro-3-methyl-2,6-dioxo-4-(trifluoromethyl)-1 (2H)-pyrimidinyl]-4-fluoro-N-[[methyl(1-methylethyl) amino] sulfonyl]benzamide (CAS: N'-{2-chloro-4-fluoro-5-[1,2,3,6-tetrahydro-3-methyl-2,6-dioxo-4-(trifluoromethyl) pyrimidin-1-yl] benzoyl}-N-isopropyl-N-methylsulfamide; Reg. No.: 372137-35-4); BAS-H800). As used herein a named compound, (e.g., "saflufenacil") includes the compound (e.g., saflufenacil) as well as its salts and esters, unless expressly stated otherwise.

The herbicidal compositions can also comprise auxiliary ingredients that are customary for the formulation of crop protection agents.

Examples of auxiliaries customary for the formulation of crop protection agents include inert auxiliaries, solid carriers, surfactants (such as dispersants, protective colloids, emulsifiers, wetting agents, and tackifiers), organic and inorganic thickeners, penetrants (such as penetration-enhancing organosilicone surfactants or acidic sulfate chelates, e.g., CT-301™ available from Cheltec, Inc.), safeners, bactericides, antifreeze agents, antifoams, colorants, and adhesives. Formulations of the herbicide compositions useful herein can be prepared according to any method known to be useful for that purpose in the art.

Examples of thickeners (i.e. compounds that impart modified flow properties, i.e. high viscosity in the state of rest and low viscosity in motion) are polysaccharides, such as xanthan gum (Kelzan® from Kelco), Rhodopol® 23 (Rhone Poulenc) or Veegum® (from R.T. Vanderbilt), and also organic and inorganic sheet minerals, such as Attaclay® (from Engelhard).

Examples of antifoams are silicone emulsions (for example, Silikon® SRE, Wacker or Rhodorsil® from Rhodia), long-chain alcohols, fatty acids, salts of fatty acids, organofluorine compounds, and mixtures thereof.

Bactericides can optionally be added for stabilizing the aqueous herbicidal formulations. Examples of bactericides are bactericides based on diclorophen and benzyl alcohol hemiformal (Proxel® from ICI or Acticide® RS from Thor Chemie and Kathon® MK from Rohm & Haas), and also isothiazolinone derivatives, such as alkylisothiazolinones and benzisothiazolinones (Acticide MBS from Thor Chemie).

Examples of antifreeze agents are ethylene glycol, propylene glycol, urea, and glycerol.

Examples of colorants include members of colorant classes such as the sparingly water-soluble pigments and the water-soluble dyes. Some examples include the dyes known under the names Rhodamin B, C.I. Pigment Red 112, C.I. Solvent Red 1, pigment blue 15:4, pigment blue 15:3, pigment blue 15:2, pigment blue 15:1, pigment blue 80, pigment yellow 1, pigment yellow 13, pigment red 112, pigment red 48:2, pigment red 48:1, pigment red 57:1, pigment red 53:1, pigment orange 43, pigment orange 34, pigment orange 5, pigment green 36, pigment green 7, pigment white 6, pigment brown 25, basic violet 10, basic violet 49, acid red 51, acid red 52, acid red 14, acid blue 9, acid yellow 23, basic red 10, and basic red 108.

Examples of adhesives are polyvinylpyrrolidone, polyvinyl acetate, polyvinyl alcohol and tylose.

Suitable inert auxiliaries are, for example, the following: mineral oil fractions of medium to high boiling point, such as kerosene and diesel oil; coal tar oils; oils of vegetable or animal origin; aliphatic, cyclic and aromatic hydrocarbons, for example paraffins, tetrahydronaphthalene, alkylated naphthalenes and their derivatives, alkylated benzenes and their derivatives, alcohols such as methanol, ethanol, propanol, butanol and cyclohexanol, ketones such as cyclohexanone or strongly polar solvents, for example amines such as N-methylpyrrolidone, and water.

Suitable carriers include liquid and solid carriers.

Liquid carriers include e.g. non-aqueous solvents such as cyclic and aromatic hydrocarbons, e.g. paraffins, tetrahydronaphthalene, alkylated naphthalenes and their derivatives, alkylated benzenes and their derivatives, alcohols such as methanol, ethanol, propanol, butanol and cyclohexanol, ketones such as cyclohexanone, strongly polar solvents, e.g. amines such as N-methylpyrrolidone, and water, as well as mixtures thereof.

Solid carriers include e.g. mineral earths such as silicas, silica gels, silicates, talc, kaolin, limestone, lime, chalk, bole, loess, clay, dolomite, diatomaceous earth, calcium sulfate, magnesium sulfate and magnesium oxide, ground synthetic materials, fertilizers such as ammonium sulfate, ammonium phosphate, ammonium nitrate and ureas, and products of vegetable origin, such as cereal meal, tree bark meal, wood meal, nutshell meal, cellulose powders, and other solid carriers.

Suitable surfactants (e.g., adjuvants, wetting agents, tackifiers, dispersants, or emulsifiers) include the alkali metal salts, alkaline earth metal salts and ammonium salts of aromatic sulfonic acids, for example lignosulfonic acids (e.g. Borrespers-types, Borregaard), phenolsulfonic acids, naphthalenesulfonic acids (Morwet types, Akzo Nobel) and dibutylnaphthalenesulfonic acid (Nekal types, BASF AG), and of fatty acids, alkyl- and alkylarylsulfonates, alkyl sulfates, lauryl ether sulfates and fatty alcohol sulfates, and salts of sulfated hexa-, hepta- and octadecanols, and also of fatty alcohol glycol ethers, condensates of sulfonated naphthalene and its derivatives with formaldehyde, condensates of naphthalene or of the naphthalenesulfonic acids with phenol and formaldehyde, polyoxyethylene octylphenol ether, ethoxylated isooctyl-, octyl- or nonylphenol, alkylphenyl or tributylphenyl polyglycol ether, alkylaryl polyether alcohols, isotridecyl alcohol, fatty alcohol/ethylene oxide condensates, ethoxylated castor oil, polyoxyethylene alkyl ethers or polyoxypropylene alkyl ethers, lauryl alcohol polyglycol ether acetate, sorbitol esters, lignosulfite waste liquors and proteins, denatured proteins, polysaccharides (e.g. methylcellulose), hydrophobically modified starches, polyvinyl alcohol (Mowiol types, Clariant), polycarboxylates (BASF AG, Sokalan types), polyalkoxylates, polyvinylamine (BASF AG, Lupamine types), polyethyleneimine (BASF AG, Lupasol types), polyvinylpyrrolidone and copolymers thereof.

Powders, materials for broadcasting and dusts can be prepared by mixing or concomitant grinding of the A.I.s together with a solid carrier.

Granules, for example coated granules, impregnated granules and homogeneous granules, can be prepared by binding the A.I.s to solid carriers.

Aqueous use forms can be prepared from emulsion concentrates, suspensions, pastes, wettable powders or water-dispersible granules by adding water.

To prepare emulsions, pastes or oil dispersions, the herbicidal compositions can be homogenized in water by means of a wetting agent, tackifier, dispersant or emulsifier. Alternatively, it is also possible to prepare concentrates comprising active compound, wetting agent, tackifier, dispersant or emulsifier and, if desired, solvent or oil, preferably suitable for dilution or dispersion with water.

The concentration of the herbicide(s) present in the herbicidal composition can be varied within wide ranges. In general, the formulations comprise approximately from 0.001% to 98% by weight, preferably 0.01 to 95% by weight of at least one active ingredient. In some embodiments, the A.I.s are employed in a purity of from 90% to 100%, preferably 95% to 100% (measured, e.g., according to NMR or IR spectra).

In some formulations, the herbicides are suspended, emulsified, or dissolved. The formulations may be in the form of aqueous solutions, powders, suspensions, or highly-concentrated aqueous, oily or other suspensions or dispersions, aqueous emulsions, aqueous microemulsions, aqueous suspo-emulsions, oil dispersions, pastes, dusts, materials for spreading, or granules.

The herbicides or the herbicidal compositions comprising them can be applied pre-emergence, post-emergence or pre-planting, or together with the seed. It is also possible to apply the herbicidal composition or active compounds by planting seed pretreated with the herbicidal compositions or active compounds.

In a further embodiment, the herbicides or herbicidal compositions can be applied by treating seed. The treatment of seeds comprises essentially any of the procedures familiar to the person skilled in the art (e.g., seed dressing, seed coating, seed dusting, seed soaking, seed film coating, seed multilayer coating, seed encrusting, seed dripping and seed pelleting). The herbicidal compositions can be applied diluted or undiluted.

It may furthermore be beneficial to apply the herbicides alone or in combination with other herbicides, or in the form of a mixture with other crop protection agents, for example together with agents for controlling pests or phytopathogenic fungi or bacteria. Also of interest is the miscibility with mineral salt solutions, which are employed for treating nutritional and trace element deficiencies. Other additives such as non-phytotoxic oils and oil concentrates can also be added.

Moreover, it may be useful to apply the herbicides in combination with safeners. Safeners are compounds that prevent or reduce herbicide-induced injury to useful plants without having a major impact on the herbicidal action of the herbicides. They can be applied either before sowing (e.g. on seed treatments, shoots or seedlings) or in the pre-emergence application or post-emergence application of the crop plant. The safeners and the herbicides can be applied simultaneously or in succession.

Safeners include e.g. (quinolin-8-oxy)acetic acids, 1-phenyl-5-haloalkyl-1H-1,2,4-triazol-3-carboxylic acids, 1-phenyl-4,5-dihydro-5-alkyl-1H-pyrazol-3,5-dicarboxylic acids, 4,5-dihydro-5,5-diaryl-3-isoxazol carboxylic acids, dichloroacetamides, alpha-oximinophenylacetonitriles, acetophenonoximes, 4,6-dihalo-2-phenylpyrimidines, N-[[4-(aminocarbonyl)phenyl]sulfonyl]-2-benzoic amides, 1,8-naphthalic anhydride, 2-halo-4-(haloalkyl)-5-thiazol carboxylic acids, benoxacor, cloquintocet, cyometrinil, cyprosulfamide, dichlormid, dicyclonon, dietholate, fenchlorazole, fenclorim, flurazole, fluxofenim, furilazole, isoxadifen, mefenpyr, mephenate, naphthalic anhydride, oxabetrinil, 4-(dichloroacetyl)-1-oxa-4-azaspiro[4.5]decane (MON4660, CAS 71526-07-3) and 2,2,5-trimethyl-3-(dichloroacetyl)-1,3-oxazolidine (R-29148, CAS 52836-31-4), phosphorthiolates and N-alkyl-O-phenyl-carbamates and their agriculturally acceptable salts and their agriculturally acceptable derivatives such amides, esters, and thioesters.

Those skilled in the art will recognize that some compounds used as herbicides, safeners, etc. are capable of forming geometric isomers, for example E/Z isomers, enantiomers, diastereomers, or other stereoisomers. In general, it is possible to use either pure isomers or mixtures of isomers. For example, some of the aryloxyphenoxy propionate herbicides are chiral, and some of them are commonly used in enantiomerically enriched or enantiopure form, e.g. clodinafop, cyhalofop, fenoxaprop-P, fluazifop-P, haloxyfop-P, metamifop, propaquizafop or quizalofop-P. As a further example, glufosinate may be used in enantiomerically enriched or enantiopure form, also known as glufosinate-P. Alternatively, the compounds may be used in racemic mixtures or other mixtures of geometric isomers.

Controlling Weeds

Rice plants of the invention can be used in conjunction with herbicide(s) to which they are tolerant. Herbicides can be applied to the rice plants of the invention using any techniques known to those skilled in the art. Herbicides can be applied at any point in the rice plant cultivation process. For example, herbicides can be applied pre-planting, at planting, pre-emergence, post-emergence or combinations thereof. Herbicides may be applied to seeds and dried to form a layer on the seeds.

In some embodiments, seeds are treated with a safener, followed by a post-emergence application of herbicide(s). In one embodiment, the post-emergence application of herbicide(s) occurs about 7 to 10 days following planting of safener-treated seeds. In some embodiments, the safener is cloquintocet, dichlormid, fluxofenim, or combinations thereof.

In other aspects, the present invention provides a method for controlling weeds at a locus for growth of a rice plant or plant part thereof, the method comprising applying a composition comprising herbicide(s) to the locus.

In some aspects, the present invention provides a method for controlling weeds at a locus for growth of a plant, the method comprising applying a herbicide composition to the locus; wherein said locus is: (a) a locus that contains a rice plant or seed capable of producing a rice plant; or (b) a locus that will contain the rice plant or the seed after applying the herbicide composition.

The following are non-limiting examples describing different rice culturing methods including the application of herbicide(s).

In the post-flood, post-emergence (transplanted) method, rice is grown to about the 2-4 leaf stage away from the field. The field is flooded and tilled (puddled) until a blend of mud is achieved. The rice plants are then transplanted into the mud. Herbicide application typically takes place before or after flooding.

In the post-flood, post-emergence (water-seeded) method, rice is soaked for about 24 hours or more, and then is sown into the surface of a shallow flooded field. Herbicide application is typically made after weed germination.

In the pre-flood, post-emergence, direct-seeded (broadcast or drilled) method, rice is broadcast or planted with a planter under the soil surface. The field may be flushed (watered) to promote rice growth. The field is flooded about a week or more after the planting as the plants germinate. Herbicide application takes place typically before the flood, but after emergence of the rice plants.

In the pre-flood, post-emergence (Southeast Asia style) method, rice is soaked for about 24 hours or more. The field is puddled to the right consistency and drained. The pre-germinated seeds are then broadcast to the surface of the soil. Flooding takes place as the rice develops. Herbicide application normally takes place before the flooding, but after the emergence of the rice plants.

In the pre-emergence or delayed pre-emergence method, seeds are planted, usually with a planter. Herbicide is applied before emergence of the rice or weeds.

Herbicide compositions can be applied, e.g., as foliar treatments, soil treatments, seed treatments, or soil drenches. Application can be made, e.g., by spraying, dusting, broadcasting, or any other mode known in the art.

In one embodiment, herbicides can be used to control the growth of weeds that may be found growing in the vicinity of the rice plants of the invention. In embodiments of this type, a herbicide to which the rice plant of the invention is tolerant can be applied to the plot at a concentration sufficient to kill or inhibit the growth of weeds. Concentrations of herbicide sufficient to kill or inhibit the growth of weeds are known in the art.

In another embodiment, the present invention provides a method for controlling weeds in the vicinity of rice plants. The method comprises applying an effective amount of herbicide(s) to the weeds and to the rice plant, wherein the rice plant has increased tolerance to the herbicide(s) when compared to a wild-type rice plant.

In another aspect, herbicide(s) can be used as a seed treatment. In some embodiments, an effective concentration or an effective amount of herbicide(s), or a composition comprising an effective concentration or an effective amount of herbicide(s) can be applied directly to the seeds prior to or during the sowing of the seeds. Seed treatment formulations may additionally comprise binders, and optionally colorants as well.

Binders can be added to improve the adhesion of the active materials onto the seeds after treatment. Suitable binders include, e.g., block copolymers, EO/PO surfactants, polyvinylalcohols, polyvinylpyrrolidones, polyacrylates, polymethacrylates, polybutenes, polyisobutylenes, polystyrene, polyethyleneamines, polyethyleneamides, polyethyleneimines (e.g., Lupasol®, Polymin®), polyethers, polyurethanes, polyvinylacetate, tylose, and copolymers derived from these polymers.

The term "seed treatment" includes all suitable seed treatment techniques known in the art, such as seed dressing, seed coating, seed dusting, seed soaking, and seed pelleting. Soil may be treated by applying a formulation containing the herbicide (e.g., a granular formulation), for example with a seed drill, with optionally one or more solid or liquid, agriculturally acceptable carriers, and optionally with one or more agriculturally acceptable surfactants.

The present invention also comprises seeds coated with or containing a seed treatment formulation comprising herbicide(s).

The term "coated with or containing" generally signifies that the active ingredient is for the most part on the surface of the seed at the time of application, although a greater or lesser part of the ingredient may penetrate into the seed, depending on the method of application. When the seed is planted, it may absorb the active ingredient.

In some embodiments, the seed treatment with herbicide(s) or with a formulation comprising the herbicide(s) is applied by spraying or dusting the seeds, or otherwise treating the seeds, before the seeds are sown.

In other aspects, the present invention provides a method for combating undesired vegetation or controlling weeds, comprising contacting seeds of the rice plants with herbicide(s) before sowing, or after pre-germination, or both. The method can further comprise sowing the seeds, for example, in soil in a field or in a potting medium in a greenhouse. The method finds particular use in combating undesired vegetation or controlling weeds in the immediate vicinity of the seed. The control of undesired vegetation is understood as the killing of weeds, or otherwise retarding or inhibiting the normal growth of weeds. Weeds, in the broadest sense, are understood as meaning all those plants that grow in locations where they are undesired.

The weeds that may be treated include, for example, dicotyledonous and monocotyledonous weeds. Monocotyledonous weeds include, but are not limited to, weeds of the genera: *Echinochloa, Setaria, Panicum, Digitaria, Phleum, Poa, Festuca, Eleusine, Brachiaria, Lolium, Bromus, Avena, Oryza, Cyperus, Sorghum, Agropyron, Cynodon, Monochoria, Fimbristyslis, Sagittaria, Eleocharis, Scirpus, Paspalum, Ischaemum, Sphenoclea, Dactyloctenium, Agrostis, Alopecurus,* and *Apera.* Dicotyledonous weeds include, but are not limited to, weeds of the genera: *Sinapis, Lepidium, Galium, Stellaria, Matricaria, Anthemis, Galinsoga, Chenopodium, Urtica, Senecio, Amaranthus, Portulaca, Xanthium, Convolvulus, Ipomoea, Polygonum, Sesbania, Ambrosia, Cirsium, Carduus, Sonchus, Solanum, Rorippa, Rotala, Lindernia, Lamium, Veronica, Abutilon, Emex, Datura, Viola, Galeopsis, Papaver, Centaurea, Trifolium, Ranunculus,* and *Taraxacum.*

Examples of red/weedy rice include, but are not limited to, *Oryza longistaminata, Oryza sativa* L. var. *sylvatica, Oryza latifolia, Oryza barthii* A. Chev, *Oryza punctata,* and *Oryza rufipogon.*

Examples of *Echinochloa* spp. include, but are not limited to, *Echinochloa colona, Echinochloa crusgalli,* and *Echinochloa oryzicola.*

In addition, the weeds treated with the present invention can include, for example, crop plants that are growing in an undesired location.

In still further aspects, loci, plants, plant parts, or seeds are treated with an agronomically acceptable composition that does not contain an A.I. For example, the treatment may comprise one or more agronomically-acceptable carriers, diluents, excipients, plant growth regulators, and the like; or an adjuvant, such as a surfactant, a spreader, a sticker, a penetrant, a drift-control agent, a crop oil, an emulsifier, a compatibility agent, or combinations thereof.

In other aspects, the present invention provides a product prepared from the rice plants of the invention, for example, brown rice (e.g., cargo rice), broken rice (e.g., chits, brewer's rice), polished rice (e.g., milled rice), rice hulls (e.g., husks, chaff), rice bran, rice pollards, rice mill feed, rice flour, rice oil, oiled rice bran, de-oiled rice bran, arrak, rice wine, poultry litter, and animal feed.

Further Embodiments of the Invention

As used herein, the term "plant" includes plant cells, plant protoplasts, plant cells of tissue culture from which rice plants can be regenerated, plant calli, plant clumps, and plant cells that are intact in plants or parts of plants, such as pollen, flowers, embryos, ovules, seeds, pods, leaves, stems, roots, anthers and the like. Thus, another aspect of this invention is to provide for cells that, upon growth and differentiation, produce a cultivar having essentially all of the physiological and morphological characteristics of 'CL271.'

Techniques for transforming with and expressing desired structural genes and cultured cells are known in the art. Also, as known in the art, rice may be transformed and regenerated such that whole plants containing and expressing desired genes under regulatory control are obtained. General descriptions of plant expression vectors and reporter genes and transformation protocols can be found, for example, in Gruber et al., "Vectors for Plant Transformation, in Methods in Plant Molecular Biology & Biotechnology" in Glich et al. (Eds. pp. 89-119, CRC Press, 1993). For example, expression vectors and gene cassettes with the GUS reporter are available from Clone Tech Laboratories, Inc. (Palo Alto, Calif.), and expression vectors and gene cassettes with luciferase reporter are available from Promega Corp. (Madison, Wis.). General methods of culturing plant tissues are provided, for example, by Maki et al., "Procedures for Introducing Foreign DNA into Plants" in Methods in Plant Molecular Biology & Biotechnology, Glich et al., (Eds. pp. 67-88 CRC Press, 1993); by Phillips et al., "Cell-Tissue Culture and In-Vitro Manipulation" in Corn & Corn Improvement, 3rd Edition; and by Sprague et al., (Eds. pp. 345-387) American Society of Agronomy Inc., 1988. Methods of introducing expression vectors into plant tissue include the direct infection or co-cultivation of plant cells with *Agrobacterium tumefaciens*, Horsch et al., *Science*, 227:1229 (1985). Descriptions of *Agrobacterium* vectors systems and methods for *Agrobacterium*-mediated gene transfer are provided by Gruber et al., supra.

Useful methods include but are not limited to expression vectors introduced into plant tissues using a direct gene transfer method such as microprojectile-mediated delivery, DNA injection, electroporation and the like. More preferably expression vectors are introduced into plant tissues using the microprojectile media delivery with biolistic device- or *Agrobacterium*-mediated transformation. Transformed plants obtained with the germplasm of 'CL271' are intended to be within the scope of this invention.

The present invention also provides rice plants regenerated from a tissue culture of the 'CL271' variety or hybrid plant. As is known in the art, tissue culture can be used for the in vitro regeneration of a rice plant. For example, see Chu, Q. R. et al. (1999) "Use of bridging parents with high anther culturability to improve plant regeneration and breeding value in rice," *Rice Biotechnology Quarterly*, 38:25-26; Chu, Q. R. et al., "A novel plant regeneration medium for rice anther culture of Southern U.S. crosses," *Rice Biotechnology Quarterly*, 35:15-16 (1998); Chu, Q. R. et al., "A novel basal medium for embryogenic callus induction of Southern US crosses," *Rice Biotechnology Quarterly*, 32:19-20 (1997); and Oono, K., "Broadening the Genetic Variability By Tissue Culture Methods," *Jap. J. Breed.,* 33 (Supp. 2), 306-307 (1983). Thus, another aspect of this invention is to provide cells that, upon growth and differentiation, produce rice plants having all, or essentially all, of the physiological and morphological characteristics of variety 'CL271.'

Unless context clearly indicates otherwise, references in the specification and claims to 'CL271' should be understood also to include single gene conversions of 'CL271' with a gene encoding a trait such as, for example, male sterility, other sources of herbicide resistance, resistance for bacterial, fungal, or viral disease, insect resistance, male fertility, enhanced nutritional quality, industrial usage, yield stability and yield enhancement.

Duncan et al., *Planta,* 165:322-332 (1985) reflects that 97% of the plants cultured that produced callus were capable of plant regeneration. Subsequent experiments with both inbreds and hybrids produced 91% regenerable callus that produced plants. In a further study, Songstad et al., *Plant Cell Reports,* 7:262-265 (1988) reported several media additions that enhanced regenerability of callus of two inbred lines. Other published reports also indicate that "nontraditional" tissues are capable of producing somatic embryogenesis and plant regeneration. K. P. Rao et al., *Maize Genetics Cooperation Newsletter,* 60:64-65 (1986), refers to somatic embryogenesis from glume callus cultures and B. V. Conger et al., *Plant Cell Reports,* 6:345-347 (1987) reported somatic embryogenesis from the tissue cultures of corn leaf segments. These methods of obtaining plants are routinely used with a high rate of success.

Tissue culture of corn (maize) is described in European Patent Application No. 160,390. Corn tissue culture procedures, which may be adapted for use with rice, are also described in Green et al., "Plant Regeneration in Tissue Culture of Maize," *Maize for Biological Research* (Plant Molecular Biology Association, Charlottesville, Va., pp. 367-372, 1982) and in Duncan et al., "The Production of Callus Capable of Plant Regeneration from Immature Embryos of Numerous *Zea Mays* Genotypes," 165 *Planta,* 322:332 (1985). Thus, another aspect of this invention is to provide cells that, upon growth and differentiation, produce rice plants having all, or essentially all, of the physiological and morphological characteristics of hybrid rice line 'CL271.' See T. P. Croughan et al., (Springer-Verlag, Berlin, 1991) Rice (*Oryza sativa.* L): Establishment of Callus Culture and the regeneration of Plants, in *Biotechnology in Agriculture and Forestry* (19-37).

With the advent of molecular biological techniques that allow the isolation and characterization of genes that encode specific protein products, it is now possible to routinely engineer plant genomes to incorporate and express foreign genes, or additional or modified versions of native, or endogenous, genes (perhaps driven by different promoters) in order to alter the traits of a plant in a specific manner. Such foreign, additional, and modified genes are herein referred to collectively as "transgenes." In recent years, several methods for producing transgenic plants have been developed, and the present invention, in particular embodiments, also relates to transformed versions of 'CL271.'

An expression vector is constructed that will function in plant cells. Such a vector comprises a DNA coding sequence that is under the control of or is operatively linked to a regulatory element (e.g., a promoter). The expression vector may contain one or more such operably linked coding sequence/regulatory element combinations. The vector(s) may be in the form of a plasmid or virus, and can be used alone or in combination with other plasmids or viruses to provide transformed rice plants.

Expression Vectors

Expression vectors commonly include at least one genetic "marker," operably linked to a regulatory element (e.g., a promoter) that allows transformed cells containing the marker to be either recovered by negative selection, i.e., inhibiting growth of cells that do not contain the selectable marker gene, or by positive selection, i.e., screening for the product encoded by the genetic marker. Many commonly used selectable marker genes for plant transformation are known in the art, and include, for example, genes that code for enzymes that metabolically detoxify a selective chemical inhibitor such as an antibiotic or a herbicide, or genes that encode an altered target that is insensitive to such an inhibitor. Positive selection methods are also known in the art.

For example, a commonly used selectable marker gene for plant transformation is that for neomycin phosphotransferase II (nptII), isolated from transposon Tn5, whose expression confers resistance to kanamycin. See Fraley et al., *Proc. Natl. Acad. Sci. U.S.A.,* 80:4803 (1983). Another commonly used selectable marker gene is the hygromycin phosphotransferase gene, which confers resistance to the antibiotic hygromycin. See Vanden Elzen et al., *Plant Mol. Biol.,* 5:299 (1985).

Additional selectable marker genes of bacterial origin that confer resistance to one or more antibiotics include gentamycin acetyl transferase, streptomycin phosphotransferase, aminoglycoside-3'-adenyl transferase, and the bleomycin resistance determinant. Hayford et al., *Plant Physiol.,* 86:1216 (1988), Jones et al., *Mol. Gen. Genet.,* 210:86 (1987), Svab et al., *Plant Mol. Biol.,* 14:197 (1990); *Plant Mol. Biol.,* 7:171 (1986). Other selectable marker genes confer resistance to herbicides such as glyphosate, glufosinate, or broxynil. Comai et al., *Nature,* 317:741-744 (1985); Gordon-Kamm et al., *Plant Cell,* 2:603-618 (1990); and Stalker et al., *Science,* 242:419-423 (1988).

Selectable marker genes for plant transformation of non-bacterial origin include, for example, mouse dihydrofolate reductase, plant 5-enolpyruvylshikimate-3-phosphate synthase, and plant acetolactate synthase. Eichholtz et al., *Somatic Cell Mol. Genet.* 13:67 (1987); Shah et al., *Science,* 233:478 (1986); and Charest et al., *Plant Cell Rep.,* 8:643 (1990).

Another class of marker genes for plant transformation employs screening of presumptively transformed plant cells, rather than selection for resistance to a toxic substance such as an antibiotic. These marker genes are particularly useful to quantify or visualize the spatial pattern of expression of a gene in specific tissues, and are frequently referred to as reporter genes because they may be fused to the target gene or regulatory sequence. Commonly used reporter genes include glucuronidase (GUS), galactosidase, luciferase, chloramphenicol, and acetyltransferase. See Jefferson, R. A., *Plant Mol. Biol. Rep.,* 5:387 (1987); Teeri et al., *EMBO J.,* 8:343 (1989); Koncz et al., *Proc. Natl. Acad. Sci. U.S.A.,* 84:131 (1987); and DeBlock et al., *EMBO J.,* 3:1681 (1984). Another approach to identifying relatively rare transformation events has been the use of a gene that encodes a dominant constitutive regulator of the *Zea mays* anthocyanin pigmentation pathway. Ludwig et al., *Science,* 247:449 (1990).

The Green Fluorescent Protein (GFP) gene has been used as a marker for gene expression in prokaryotic and eukaryotic cells. See Chalfie et al., *Science,* 263:802 (1994). GFP and mutants of GFP may be used as screenable markers.

Genes included in expression vectors are driven by a nucleotide sequence comprising a regulatory element, for example, a promoter. Many suitable promoters are known in the art, as are other regulatory elements that may be used either alone or in combination with promoters.

As used herein, "promoter" refers to a region of DNA upstream or downstream from the transcription initiation site, a region that is involved in recognition and binding of RNA polymerase and other proteins to initiate transcription. A "plant promoter" is a promoter capable of initiating transcription in plant cells. Examples of promoters under developmental control include promoters that preferentially initiate transcription in certain tissues, such as leaves, roots, seeds, fibers, xylem vessels, tracheids, or sclerenchyma. Such promoters are referred to as "tissue-preferred." Promoters that initiate transcription only in certain tissue are referred to as "tissue-specific." A "cell type" specific promoter primarily drives expression in certain cell types in one or more organs, for example, vascular cells in roots or leaves. An "inducible" promoter is a promoter that is under environmental control. Examples of environmental conditions that may induce transcription by inducible promoters include anaerobic conditions or the presence of light. Tissue-specific, tissue-preferred, cell type specific, and inducible promoters are examples of "non-constitutive" promoters. A "constitutive" promoter is a promoter that is generally active under most environmental conditions.

A. Inducible Promoters

An inducible promoter is operably linked to a gene for expression in rice. Optionally, the inducible promoter is operably linked to a nucleotide sequence encoding a signal sequence that is operably linked to a gene for expression in rice. With an inducible promoter the rate of transcription increases in response to an inducing agent.

Any suitable inducible promoter may be used in the present invention. See Ward et al., *Plant Mol. Biol.,* 22:361-366 (1993). Examples include those from the ACEI system, which responds to copper, Meft et al., *PNAS,* 90:4567-4571 (1993); In2 gene from maize, which responds to benzenesulfonamide herbicide safeners, Hershey et al., *Mol. Gen Genetics,* 227:229-237 (1991); Gatz et al., *Mol. Gen. Genetics,* 243:32-38 (1994); and Tet repressor from Tn10, Gatz, *Mol. Gen. Genetics,* 227:229-237 (1991). A preferred inducible promoter is one that responds to an inducing agent to which plants do not normally respond, for example, the inducible promoter from a steroid hormone gene, the transcriptional activity of which is induced by a glucocorticosteroid hormone. See Schena et al., *Proc. Natl. Acad. Sci., U.S.A.* 88:0421 (1991).

B. Constitutive Promoters

A constitutive promoter is operably linked to a gene for expression in rice, or the constitutive promoter is operably linked to a nucleotide sequence encoding a signal sequence that is operably linked to a gene for expression in rice.

Constitutive promoters may also be used in the instant invention. Examples include promoters from plant viruses such as the 35S promoter from cauliflower mosaic virus, Odell et al., *Nature,* 313:810-812 (1985), and the promoters from the rice actin gene, McElroy et al., *Plant Cell,* 2:163-171 (1990); ubiquitin, Christensen et al., *Plant Mol. Biol.,* 12:619-632 (1989) and Christensen et al., *Plant Mol. Biol.* 18:675-689 (1992); pEMU, Last et al., *Theor. Appl. Genet.,* 81:581-588 (1991); MAS, Velten et al., *EMBO J.,* 3:2723-2730 (1984); and maize H3 histone, Lepetit et al., *Mol. Gen. Genetics,* 231:276-285 (1992) and Atanassova et al., *Plant Journal,* 2 (3): 291-300 (1992).

An ALS (AHAS) promoter, such as the Xba1/NcoI fragment 5' from the *Brassica napus* ALS3 structural gene (or a nucleotide sequence homologous to or otherwise similar to said Xba1/NcoI fragment), may be used as a constitutive promoter. See PCT Application WO 96/30530. The promoter from a rice ALS (AHAS) gene may also be used. See the sequences disclosed in PCT Application WO 01/85970; and U.S. Pat. No. 6,943,280.

C. Tissue-Specific or Tissue-Preferred Promoters

A tissue-specific promoter is operably linked to a gene for expression in rice. Optionally, the tissue-specific promoter is operably linked to a nucleotide sequence encoding a signal sequence that is operably linked to a gene for expression in rice. Transformed plants produce the expression product of the transgene exclusively, or preferentially, in specific tissue(s).

Any tissue-specific or tissue-preferred promoter may be used in the instant invention. Examples of tissue-specific or tissue-preferred promoters include those from the phaseolin gene, Murai et al., *Science,* 23:476-482 (1983), and Sengupta-Gopalan et al., *Proc. Natl. Acad. Sci. U.S.A.,* 82:3320-3324 (1985); a leaf-specific and light-induced promoter such as that from cab or rubisco, Simpson et al., *EMBO J.,* 4(11):2723-2729 (1985) and Timko et al., *Nature,* 318:579-582 (1985); an anther-specific promoter such as that from LAT52, Twell et al., *Mol. Gen. Genetics,* 217:240-245 (1989); a pollen-specific promoter such as that from Zm13, Guerrero et al., *Mol. Gen. Genetics,* 244:161-168 (1993); or a microspore-preferred promoter such as that from apg, Twell et al., *Sex. Plant Reprod.,* 6:217-224 (1993).

Signal Sequences for Targeting Proteins to Subcellular Compartments

Transport of protein or peptide molecules produced by transgenes to a subcellular compartment such as a chloroplast, vacuole, peroxisome, glyoxysome, cell wall, or mitochondrion, or for secretion into an apoplast, is accomplished by operably linking a nucleotide sequence encoding a signal sequence to the 5' or 3' end of a gene encoding the protein or peptide of interest. Targeting sequences at the 5' or 3' end of the structural gene may determine, during protein synthesis and processing, where the encoded protein is ultimately compartmentalized.

Many signal sequences are known in the art. See, for example, Becker et al., *Plant Mol. Biol.,* 20:49 (1992); Close, P. S., Master's Thesis, Iowa State University (1993); Knox, C. et al., "Structure and Organization of Two Divergent Alpha-Amylase Genes from Barley," *Plant Mol. Biol.,* 9:3-17 (1987); Lerner et al., *Plant Physiol.,* 91:124-129 (1989); Fontes et al., *Plant Cell,* 3:483-496 (1991); Matsuoka et al., *Proc. Natl. Acad. Sci.,* 88:834 (1991); Gould et al., *J. Cell. Biol.,* 108:1657 (1989); Creissen et al., *Plant J.,* 2:129 (1991); Kalderon et al., "A short amino acid sequence able to specify nuclear location," *Cell,* 39:499-509 (1984); and Steifel et al., "Expression of a maize cell wall hydroxyproline-rich glycoprotein gene in early leaf and root vascular differentiation," *Plant Cell,* 2:785-793 (1990).

Foreign Protein Genes and Agronomic Genes

Agronomically significant genes that may be transformed into rice plants in accordance with the present invention include, for example, the following:

1. Genes that Confer Resistance to Pests or Disease:
    A. Plant disease resistance genes. Plant defenses are often activated by specific interaction between the product of a disease resistance gene (R) in the plant and the product of a corresponding avirulence (Avr) gene in the pathogen. A plant may be transformed with a cloned resistance gene to engineer plants that are resistant to specific pathogen strains. See, e.g., Jones et al., *Science* 266:789 (1994) (cloning of the tomato Cf-9 gene for resistance to *Cladosporium fulvum*); Martin et al., *Science* 262:1432 (1993) (tomato Pto gene for resistance to *Pseudomonas syringae* pv. Tomato encodes a protein kinase); and Mindrinos et al., *Cell* 78:1089 (1994) (*Arabidopsis* RSP2 gene for resistance to *Pseudomonas syringae*).
    B. A *Bacillus thuringiensis* protein, a derivative thereof, or a synthetic polypeptide modeled thereon. See, e.g., Geiser et al., *Gene* 48:109 (1986), disclosing the cloning and nucleotide sequence of a Bt-endotoxin gene. DNA molecules encoding endotoxin genes may be obtained from American Type Culture Collection, Manassas, Va., e.g., under ATCC Accession Nos. 40098, 67136, 31995, and 31998.
    C. A lectin. See, for example, Van Damme et al., *Plant Molec. Biol.* 24:25 (1994), disclosing the nucleotide sequences of several *Clivia miniata* mannose-binding lectin genes.
    D. A vitamin-binding protein such as avidin. See PCT Application US93/06487. This disclosure teaches the use of avidin and avidin homologues as larvicides against insect pests.
    E. An enzyme inhibitor, e.g., a protease or proteinase inhibitor or an amylase inhibitor. See, e.g., Abe et al., *J. Biol. Chem.* 262:16793 (1987) (nucleotide sequence of rice cysteine proteinase inhibitor); Huub et al., *Plant Molec. Biol.* 21:985 (1993) (nucleotide sequence of cDNA encoding tobacco proteinase inhibitor 1); and Sumitani et al., *Biosci. Biotech. Biochem.* 57:1243 (1993) (nucleotide sequence of *Streptomyces nitrosporeus*-amylase inhibitor).
    F. An insect-specific hormone or pheromone such as an ecdysteroid and juvenile hormone, a variant thereof, a mimetic based thereon, or an antagonist or agonist thereof. See, e.g., Hammock et al., *Nature,* 344:458 (1990), disclosing baculovirus expression of cloned juvenile hormone esterase, an inactivator of juvenile hormone.
    G. An insect-specific peptide or neuropeptide that, upon expression, disrupts the physiology of the affected pest. See, e.g., Regan, *J. Biol. Chem.* 269:9 (1994) (expression cloning yields DNA coding for insect diuretic hormone receptor); and Pratt et al., *Biochem. Biophys. Res. Comm.,* 163:1243 (1989) (an allostatin in *Diploptera puntata*). See also U.S. Pat. No. 5,266,317 to Tomalski et al., disclosing genes encoding insect-specific, paralytic neurotoxins.
    H. An insect-specific venom produced in nature by a snake, a wasp, etc. For example, see Pang et al., *Gene,* 116:165 (1992), concerning heterologous expression in plants of a gene coding for a scorpion insectotoxic peptide.
    I. An enzyme responsible for hyperaccumulation of a monoterpene, a sesquiterpene, a steroid, hydroxamic acid, a phenylpropanoid derivative or another non-protein molecule with insecticidal activity.
    J. An enzyme involved in the modification, including post-translational modification, of a biologically active molecule; e.g., a glycolytic enzyme, a proteolytic enzyme, a lipolytic enzyme, a nuclease, a cyclase, a transaminase, an esterase, a hydrolase, a phosphatase, a kinase, a phosphorylase, a polymerase, an elastase, a chitinase, or a glucanase, either natural or synthetic. See PCT Application WO 9302197 to Scott et al., which discloses the nucleotide sequence of a callase gene. DNA molecules that contain chitinase-encoding sequences can be obtained, for example, from the American Type Culture Collection under Accession Nos. 39637 and 67152. See also Kramer et al., *Insect Biochem. Molec. Biol.* 23:691 (1993), which discloses the nucleotide sequence of a cDNA encoding tobacco hookworm chitinase; and Kawalleck et al., *Plant Molec. Biol.,* 21:673 (1993), which discloses the nucleotide sequence of the parsley ubi4-2 polyubiquitin gene.

K. A molecule that stimulates signal transduction. See, e.g., Botella et al., *Plant Molec. Biol.,* 24:757 (1994), which discloses nucleotide sequences for mung bean calmodulin cDNA clones; and Griess et al., *Plant Physiol.,* 104:1467 (1994), which discloses the nucleotide sequence of a maize calmodulin cDNA clone.

L. An antimicrobial or amphipathic peptide. See PCT Application WO 9516776 (disclosing peptide derivatives of Tachyplesin that inhibit fungal plant pathogens); and PCT Application WO 9518855 (disclosing synthetic antimicrobial peptides that confer disease resistance).

M. A membrane permease, a channel former or a channel blocker. See, e.g., Jaynes et al., *Plant Sci.,* 89:43 (1993), which discloses heterologous expression of a cecropin lytic peptide analog to render transgenic tobacco plants resistant to *Pseudomonas solanacearum.*

N. A viral-invasive protein or a complex toxin derived therefrom. For example, the accumulation of viral coat proteins in transformed plant cells induces resistance to viral infection or disease development caused by the virus from which the coat protein gene is derived, as well as by related viruses. Coat protein-mediated resistance has been conferred upon transformed plants against alfalfa mosaic virus, cucumber mosaic virus, tobacco streak virus, potato virus X, potato virus Y, tobacco etch virus, tobacco rattle virus, and tobacco mosaic virus. See Beachy et al., *Ann. Rev. Phytopathol.,* 28:451 (1990).

O. An insect-specific antibody or an immunotoxin derived therefrom. Thus, an antibody targeted to a critical metabolic function in the insect gut inactivates an affected enzyme, killing the insect. See Taylor et al., Abstract #497, Seventh Int'l Symposium on Molecular Plant-Microbe Interactions (Edinburgh, Scotland, 1994) (enzymatic inactivation in transgenic tobacco via production of single-chain antibody fragments).

P. A virus-specific antibody. See, e.g., Tavladoraki et al., *Nature,* 366:469 (1993), showing protection of transgenic plants expressing recombinant antibody genes from virus attack.

Q. A developmental-arrest protein produced in nature by a pathogen or a parasite. For example, fungal endo-1, 4-D-polygalacturonases facilitate fungal colonization and plant nutrient release by solubilizing plant cell wall homo-1,4-D-galacturonase. See Lamb et al., *Bio/Technology,* 10:1436 (1992). The cloning and characterization of a gene that encodes a bean endopolygalacturonase-inhibiting protein is described by Toubart et al., *Plant J.,* 2:367 (1992).

R. A developmental-arrest protein produced in nature by a plant. For example, Logemann et al., *Bio/Technology,* 10:305 (1992) reported that transgenic plants expressing the barley ribosome-inactivating gene have an increased resistance to fungal disease.

2. Genes that Confer Additional Resistance to a Herbicide, Beyond that which is Inherent in 'CL271,' for Example:

A. A herbicide that inhibits the growing point or meristem, such as an imidazolinone or a sulfonylurea. Exemplary genes in this category code for mutant ALS and AHAS enzymes as described, for example, by Lee et al., *EMBO J.,* 7:1241 (1988); and Miki et al., *Theor. Appl. Genet.,* 80:449 (1990), respectively. See, additionally, U.S. Pat. Nos. 5,545,822; 5,736,629; 5,773,703; 5,773,704; 5,952,553; 6,274,796; 6,943,280; 7,019,196; 7,345,221; 7,399,905; 7,495,153; 7,754,947; and 7,786,360; published International Patent Application WO 2010/059656; (currently) unpublished International Patent Applications PCT/US2010/051749, and PCT/US2010/051780; and published U.S. patent applications US 2007/0061915, US 2010/0257623, and US 2009/0025108. Resistance to AHAS-acting herbicides may be through a mechanism other than a resistant AHAS enzyme. See, e.g., U.S. Pat. No. 5,545,822.

B. Glyphosate. Resistance may be imparted by mutant 5-enolpyruvl-3-phosphikimate synthase (EPSP) and aroA genes. Other phosphono compounds such as glufosinate. Resistance may be imparted by phosphinothricin acetyl transferase, PAT and *Streptomyces hygroscopicus* phosphinothricin-acetyl transferase, bar, genes. Pyridinoxy or phenoxy propionic acids and cyclohexones. Resistance may be imparted by ACCase inhibitor-encoding genes. See, e.g., U.S. Pat. No. 4,940,835 to Shah et al., which discloses the nucleotide sequence of a form of EPSP that confers glyphosate resistance. A DNA molecule encoding a mutant aroA gene can be obtained under ATCC Accession Number 39256, and the nucleotide sequence of the mutant gene is disclosed in U.S. Pat. No. 4,769,061 to Comai. European Patent Application No. 0333033 to Kumada et al.; and U.S. Pat. No. 4,975,374 to Goodman et al., disclose nucleotide sequences of glutamine synthetase genes that confer resistance to herbicides such as L-phosphinothricin. The nucleotide sequence of a phosphinothricin-acetyltransferase gene is provided in European Application No. 0242246 to Leemans et al. and DeGreef et al., *Bio/Technology,* 7:61 (1989), describing the production of transgenic plants that express chimeric bar genes coding for phosphinothricin acetyl transferase activity. Examples of genes conferring resistance to phenoxy propionic acids and cyclohexones, such as sethoxydim and haloxyfop, are the Acc1-S1, Acc1-S2, and Acc1-S3 genes described by Marshall et al., *Theor. Appl. Genet.,* 83:435 (1992).

C. A herbicide that inhibits photosynthesis, such as a triazine (psbA and gs+ genes) or a benzonitrile (nitrilase gene). Przibilla et al., *Plant Cell,* 3:169 (1991), describe the transformation of *Chlamydomonas* with plasmids encoding mutant psbA genes. Nucleotide sequences for nitrilase genes are disclosed in U.S. Pat. No. 4,810,648 to Stalker, and DNA molecules containing these genes are available under ATCC Accession Nos. 53435, 67441, and 67442. Cloning and expression of DNA coding for a glutathione S-transferase is described by Hayes et al., *Biochem. J.,* 285:173 (1992).

3. Genes that Confer or Contribute to a Value-added Trait, such as:

A. Modified fatty acid metabolism, for example, by transforming a plant with an antisense sequence to stearyl-ACP desaturase, to increase stearic acid content of the plant. See Knultzon et al., *Proc. Natl. Acad. Sci. U.S.A.* 89:2624 (1992).

B. Decreased Phytate Content

1) Introduction of a phytase-encoding gene would enhance breakdown of phytate, adding more free phosphate to the transformed plant. See, e.g., Van Hartingsveldt et al., *Gene*, 127:87 (1993), which discloses the nucleotide sequence of an *Aspergillus niger* phytase gene.

2) A gene may be introduced to reduce phytate content. For example, this may be accomplished by cloning, and then reintroducing DNA associated with an allele that is responsible for maize mutants characterized by low levels of phytic acid, or a homologous or analogous mutation in rice may be used. See Raboy et al., *Maydica*, 35:383 (1990).

C. Carbohydrate composition may be modified, for example, by transforming plants with a gene coding for an enzyme that alters the branching pattern of starch. See Shiroza et al., *J. Bacteol.*, 170:810 (1988) (nucleotide sequence of *Streptococcus* mutant fructosyltransferase gene); Steinmetz et al., *Mol. Gen. Genet.*, 20:220 (1985) (nucleotide sequence of *Bacillus subtilis* levansucrase gene); Pen et al., *Bio/Technology*, 10:292 (1992) (production of transgenic plants that express *Bacillus lichenifonnis* amylase); Elliot et al., *Plant Molec. Biol.*, 21:515 (1993) (nucleotide sequences of tomato invertase genes); Søgaard et al., *J. Biol. Chem.*, 268:22480 (1993) (site-directed mutagenesis of barley amylase gene); and Fisher et al., *Plant Physiol.*, 102: 1045 (1993) (maize endosperm starch branching enzyme 11).

Methods for Rice Transformation

Numerous methods for plant transformation are known in the art, including both biological and physical transformation protocols. See, e.g., Miki, et al., "Procedures for Introducing Foreign DNA into Plants" in *Methods in Plant Molecular Biology and Biotechnology*; Glick B. R. and Thompson, J. E. (Eds.) (CRC Press, Inc., Boca Raton, 1993), pp. 67-88. In addition, expression vectors and in vitro culture methods for plant cell or tissue transformation and regeneration of plants are known in the art. See, e.g., Gruber et al., "Vectors for Plant Transformation" in *Methods in Plant Molecular Biology and Biotechnology*, Glick B. R. and Thompson, J. E. (Eds.) (CRC Press, Inc., Boca Raton, 1993), pp. 89-119.

A. *Agrobacterium*-Mediated Transformation

One method for introducing an expression vector into plants is based on the natural transformation system of *Agrobacterium*. See, e.g., Horsch et al., *Science*, 227:1229 (1985). *A. tumefaciens* and *A. rhizogenes* are plant pathogenic soil bacteria that genetically transform plant cells. The Ti and Ri plasmids of *A. tumefaciens* and *A. rhizogenes*, respectively, carry genes responsible for genetic transformation of plants. See, e.g., Kado, C. I., *Crit. Rev. Plant Sci.*, 10:1 (1991). Descriptions of *Agrobacterium* vector systems and methods for *Agrobacterium*-mediated gene transfer are provided by Gruber et al., supra; Miki et al., supra; and Moloney, et al., *Plant Cell Reports*, 8:238 (1989). See also U.S. Pat. No. 5,591,616.

B. Direct Gene Transfer

Despite the fact the host range for *Agrobacterium*-mediated transformation is broad, it is more difficult to transform some cereal crop species and gymnosperms via this mode of gene transfer, although success has been achieved in both rice and corn. See Hiei et al., *The Plant Journal*, 6:271-282 (1994); and U.S. Pat. No. 5,591,616. Other methods of plant transformation exist as alternatives to *Agrobacterium*-mediated transformation.

A generally applicable method of plant transformation is microprojectile-mediated (so-called "gene gun") transformation, in which DNA is carried on the surface of microprojectiles, typically 1 to 4 µm in diameter. The expression vector is introduced into plant tissues with a biolistic device that accelerates the microprojectiles to typical speeds of 300 to 600 m/s, sufficient to penetrate plant cell walls and membranes. Sanford et al., *Part. Sci. Technol.*, 5:27 (1987); Sanford, J. C., *Trends Biotech.*, 6:299 (1988); Klein et al., *Bio/Technology*, 6:559-563 (1988); Sanford, J. C., *Physiol Plant*, 7:206 (1990); and Klein et al., *Biotechnology*, 10:268 (1992). Various target tissues may be bombarded with DNA-coated microprojectiles to produce transgenic plants, including, for example, callus (Type I or Type II), immature embryos, and meristematic tissue.

Another method for physical delivery of DNA to plants is sonication of target cells. Zhang et al., *Bio/Technology*, 9:996 (1991). Alternatively, liposome or spheroplast fusion has been used to introduce expression vectors into plants. Deshayes et al., *EMBO J.*, 4:2731 (1985); and Christou et al., *Proc Natl. Acad. Sci. U.S.A.*, 84:3962 (1987). Direct uptake of DNA into protoplasts, using $CaCl_2$ precipitation, polyvinyl alcohol or poly-L-ornithine, has also been reported. Hain et al., *Mol. Gen. Genet.*, 199:161 (1985); and Draper et al., *Plant Cell Physiol.*, 23:451 (1982). Electroporation of protoplasts and whole cells and tissues has also been described. Donn et al., in Abstracts of VIIth International Congress on Plant Cell and Tissue Culture IAPTC, A2-38, p. 53 (1990); D'Halluin et al., *Plant Cell*, 4:1495-1505 (1992); and Spencer et al., *Plant Mol. Biol.*, 24:51-61 (1994).

Following transformation of rice target tissues, expression of a selectable marker gene allows preferential selection of transformed cells, tissues, or plants, using regeneration and selection methods known in the art.

These methods of transformation may be used for producing a transgenic inbred line. The transgenic inbred line may then be crossed with another inbred line (itself either transformed or non-transformed), to produce a new transgenic inbred line. Alternatively, a genetic trait that has been engineered into a particular rice line may be moved into another line using traditional crossing and backcrossing techniques. For example, backcrossing may be used to move an engineered trait from a public, non-elite inbred line into an elite inbred line, or from an inbred line containing a foreign gene in its genome into an inbred line or lines that do not contain that gene.

The term "inbred rice plant" should be understood also to include single gene conversions of an inbred line. Backcrossing methods can be used with the present invention to improve or introduce a characteristic into an inbred line.

Many single gene traits have been identified that are not regularly selected for in the development of a new inbred line, but that may be improved by crossing and backcrossing. Single gene traits may or may not be transgenic. Examples of such traits include male sterility, waxy starch, herbicide resistance, resistance for bacterial or fungal or viral disease, insect resistance, male fertility, enhanced nutritional quality, yield stability, and yield enhancement. These genes are generally inherited through the nucleus. Known exceptions to the nuclear genes include some genes for male sterility that are inherited cytoplasmically, but that still act functionally as single gene traits. Several single gene traits are described in U.S. Pat. Nos. 5,777,196; 5,948,957; and 5,969,212.

Deposit Information

A sample of seeds of the rice cultivar designated 'CL271' was deposited with the American Type Culture Collection (ATCC), 10801 University Boulevard, Manassas, Va.

20110-2209 on 15 Nov. 2013, and was assigned ATCC Accession No. PTA-120713. This deposit was made under the Budapest Treaty. In connection with the Budapest Treaty deposit, ATCC tested the deposit on 22 Nov. 2013, and ATCC confirmed that on that date the deposited seeds were viable.

Miscellaneous

The complete disclosures of all references cited in this specification are hereby incorporated by reference. Also incorporated by reference is the complete disclosure of U.S. priority application Ser. No. 61/913,451. In the event of an otherwise irreconcilable conflict, however, the present specification shall control.

What is claimed:

1. A rice seed of the variety 'CL271,' a representative sample of seed of said variety having been deposited under ATCC Accession No. PTA-120713.

2. A plant, or a part thereof, produced by growing the seed of claim 1.

3. A method for producing rice plants, said method comprising planting a plurality of rice seeds as recited in claim 1 under conditions favorable for the growth of rice plants.

4. The method of claim 3, additionally comprising the step of producing rice seed from the resulting rice plants.

5. Rice seed produced by the method of claim 4.

6. The method of claim 3, additionally comprising the step of applying herbicide in the vicinity of the rice plants to control weeds, wherein the herbicide normally inhibits acetohydroxyacid synthase, at levels of the herbicide that would normally inhibit the growth of a rice plant.

7. The method of claim 6, wherein the herbicide comprises a sulfonylurea.

8. The method of claim 6, wherein the herbicide comprises an imidazolinone.

9. The method of claim 6, wherein the herbicide comprises imazethapyr or imazamox.

10. Pollen or an ovule of the plant of claim 2.

11. A rice plant, or a part thereof, having essentially all of the physiological and morphological characteristics of the rice plant of claim 2, including the imidazolinone herbicide resistance characteristics of 'CL271.'

12. A tissue culture of regenerable cells or protoplasts produced from the rice plant of claim 2.

13. The tissue culture of claim 12, wherein said cells or protoplasts are produced from a tissue selected from the group consisting of embryos, meristematic cells, pollen, leaves, anthers, roots, root tips, flowers, seeds, and stems.

14. A rice plant regenerated from the tissue culture of claim 13, said rice plant having all or essentially all of the morphological and physiological characteristics of 'CL271,' including the imidazolinone herbicide resistance characteristics of 'CL271.'

15. A method for producing rice seed, said method comprising crossing a first parent rice plant with a second parent rice plant, and harvesting the resulting $F_1$ hybrid rice seed, wherein the first parent rice plant or the second parent rice plant is the rice plant of claim 2, wherein, if the $F_1$ hybrid rice seed is grown, then the rice plants grown from the $F_1$ hybrid rice seed will express the imidazolinone herbicide resistance characteristics of 'CL271.'

16. An $F_1$ hybrid rice seed produced by the method of claim 15, wherein, if said hybrid rice seed is grown, then the rice plants grown from said hybrid rice seed will express the imidazolinone herbicide resistance characteristics of 'CL271.'

17. The method of claim 15, additionally comprising the step of planting a plurality of the $F_1$ hybrid rice seed under conditions favorable for the growth of rice plants.

18. The method of claim 17, additionally comprising the step of producing rice seed from the resulting rice plants; wherein, if the resulting rice seed is grown, then at least some rice plants grown from the resulting rice seed will express the imidazolinone herbicide resistance characteristics of 'CL271.'

19. The method of claim 17, additionally comprising the step of applying herbicide in the vicinity of the rice plants to control weeds, wherein the herbicide normally inhibits acetohydroxyacid synthase, at levels of the herbicide that would normally inhibit the growth of a rice plant.

20. The method of claim 19, wherein the herbicide comprises a sulfonylurea.

21. The method of claim 19, wherein the herbicide comprises an imidazolinone.

22. The method of claim 19, wherein the herbicide comprises imazethapyr or imazamox.

23. A method comprising transforming the rice plant of claim 2 with a transgene, wherein the transgene confers at least one trait selected from the group consisting of: herbicide resistance, in addition to the herbicide resistance that is inherent in 'CL271' rice; insect resistance; resistance to bacterial, fungal, or viral disease; modified fatty acid metabolism; modified carbohydrate metabolism; and male sterility.

24. A herbicide resistant rice plant or part thereof, or rice seed, produced by the method of claim 23.

25. A method of introducing a desired trait into rice cultivar 'CL271,' said method comprising the steps of:
  (a) crossing plants as recited in claim 2 with plants of another rice line expressing the desired trait, to produce progeny plants;
  (b) selecting progeny plants that express the desired trait, to produce selected progeny plants;
  (c) crossing the selected progeny plants with plants as recited in claim 2 to produce new progeny plants;
  (d) selecting new progeny plants that express both the desired trait and some or all of the physiological and morphological characteristics of rice cultivar 'CL271,' to produce new selected progeny plants; and
  (e) repeating steps (c) and (d) three or more times in succession, to produce selected higher generation backcross progeny plants that express both the desired trait and essentially all of the physiological and morphological characteristics of rice cultivar 'CL271,' as described in the VARIETY DESCRIPTION INFORMATION of the specification, determined at a 5% significance level, when grown in the same environmental conditions; and wherein the selected plants express the imidazolinone herbicide resistance characteristics of 'CL271.'

26. A rice seed produced by the method of claim 25; wherein, if said rice seed is grown, then the rice plant grown from said rice seed will express the imidazolinone herbicide resistance characteristics of 'CL271.'

27. The method of claim 25, additionally comprising the step of planting a plurality of rice seed produced by selected higher generation backcross progeny plants under conditions favorable for the growth of rice plants.

28. The method of claim 27, additionally comprising the step of producing rice seed from the resulting rice plants.

29. The rice seed resulting from the method of claim 28; wherein, if the resulting rice seed is grown, then the rice plants grown from the resulting rice seed will express the imidazolinone herbicide resistance characteristics of 'CL271.'

30. The method of claim 27, additionally comprising the step of applying herbicide in the vicinity of the rice plants to control weeds, wherein the herbicide normally inhibits acetohydroxyacid synthase, at levels of the herbicide that would normally inhibit the growth of a rice plant.

31. The method of claim 30, wherein the herbicide comprises a sulfonylurea.

32. The method of claim 30, wherein the herbicide comprises an imidazolinone.

33. The method of claim 30, wherein the herbicide comprises imazethapyr or imazamox.

34. The method of claim 25, wherein the desired trait is selected from the group consisting of male sterility; herbicide resistance, in addition to the herbicide resistance that is inherent in 'CL271' rice; insect resistance; resistance to bacterial, fungal, or viral disease; modified fatty acid metabolism; and modified carbohydrate metabolism.

35. The method of claim 15, wherein, if the $F_1$ hybrid rice seed is grown, then the resulting $F_1$ hybrid rice plant will express the following characteristics:
(a) the $F_1$ hybrid rice plant expresses a mutant acetohydroxyacid synthase whose enzymatic activity is directly resistant to normally-inhibitory levels of a herbicidally-effective imidazolinone;
(b) the $F_1$ hybrid rice plant is resistant to each of the following imidazolinone herbicides, at levels of the imidazolinone herbicides that would normally inhibit the growth of a rice plant: imazethapyr, imazapic, imazaquin, imazamox, and imazapyr;
(c) the $F_1$ hybrid rice plant is resistant to each of the following sulfonylurea herbicides, at levels of the sulfonylurea herbicides that would normally inhibit the growth of a rice plant: nicosulfuron, metsulfuron methyl, thifensulfuron methyl, and tribenuron methyl; and
(d) the $F_1$ hybrid rice plant is sensitive to each of the following sulfonylurea herbicides, at levels of the sulfonylurea herbicides that would normally inhibit the growth of a rice plant: sulfometuron methyl, chlorimuron ethyl, and rimsulfuron.

36. $F_1$ hybrid rice seed produced by the method of claim 35.

37. An $F_1$ hybrid rice plant, or a part thereof, produced by growing the $F_1$ hybrid rice seed of claim 36.

38. The method of claim 36, wherein either the first parent or the second parent is male-sterile.

39. The method of claim 25, wherein:
(a) the selected higher generation backcross progeny plant expresses a mutant acetohydroxyacid synthase whose enzymatic activity is directly resistant to normally-inhibitory levels of a herbicidally-effective imidazolinone;
(b) the selected higher generation backcross progeny plant is resistant to each of the following imidazolinone herbicides, at levels of the imidazolinone herbicides that would normally inhibit the growth of a rice plant: imazethapyr, imazapic, imazaquin, imazamox, and imazapyr;
(c) the selected higher generation backcross progeny plant is resistant to each of the following sulfonylurea herbicides, at levels of the sulfonylurea herbicides that would normally inhibit the growth of a rice plant: nicosulfuron, metsulfuron methyl, thifensulfuron methyl, and tribenuron methyl; and
(d) the selected higher generation backcross progeny plant is sensitive to each of the following sulfonylurea herbicides, at levels of the sulfonylurea herbicides that would normally inhibit the growth of a rice plant: sulfometuron methyl, chlorimuron ethyl, rimsulfuron, and tribenuron methyl.

40. Rice seed harvested from selected higher generation backcross progeny plants produced by the method of claim 39; wherein, if said rice seed is grown, then the resulting hybrid rice plant will express the following characteristics:
(a) the rice plant expresses a mutant acetohydroxyacid synthase whose enzymatic activity is directly resistant to normally-inhibitory levels of a herbicidally-effective imidazolinone;
(b) the rice plant is resistant to each of the following imidazolinone herbicides, at levels of the imidazolinone herbicides that would normally inhibit the growth of a rice plant: imazethapyr, imazapic, imazaquin, imazamox, and imazapyr;
(c) the rice plant is resistant to each of the following sulfonylurea herbicides, at levels of the sulfonylurea herbicides that would normally inhibit the growth of a rice plant: nicosulfuron, metsulfuron methyl, thifensulfuron methyl, and tribenuron methyl;
(d) the rice plant is sensitive to each of the following sulfonylurea herbicides, at levels of the sulfonylurea herbicides that would normally inhibit the growth of a rice plant: sulfometuron methyl, chlorimuron ethyl, and rimsulfuron; and
(e) the rice plant expresses the desired trait.

41. A plant, or a part thereof, produced by growing the seed of claim 40.

42. A method for controlling weeds in the vicinity of rice, comprising contacting the rice with a herbicide, wherein the rice comprises either: (a) variety 'CL271,' a representative sample of seed of said variety having been deposited under ATCC Accession No. PTA-120713; or (b) an $F_1$ hybrid of 'CL271' that expresses the imidazolinone herbicide resistance characteristics of 'CL271.'

43. The method of claim 42, wherein the herbicide is an imidazolinone herbicide, a sulfonylurea herbicide, or a combination thereof.

44. The method of claim 42, wherein the rice is a rice plant and said contacting comprises applying the herbicide in the vicinity of the rice plant.

45. The method of claim 44, wherein the herbicide is applied to weeds in the vicinity of the rice plant.

46. The method of claim 42, wherein the rice is a rice seed and said contacting comprises applying the herbicide to the rice seed.

47. A method for treating rice, comprising contacting the rice with an agronomically acceptable composition containing at least one agronomically acceptable active ingredient, wherein the rice comprises either: (a) variety 'CL271,' a representative sample of seed of said variety having been deposited under ATCC Accession No. PTA-120713; or (b) an $F_1$ hybrid of 'CL271' that expresses the imidazolinone herbicide resistance characteristics of 'CL271.'

48. The method of claim 47, wherein the agronomically acceptable active ingredient is selected from the group consisting of fungicides, insecticides, antibiotics, stress tolerance-enhancing compounds, growth promoters, herbicides, molluscicides, rodenticides, animal repellants, and combinations thereof.

49. The method of claim 47, wherein the treated rice is rice seed, and wherein said contacting comprises applying an imidazolinone herbicide to the rice seed.

50. The method of claim 43, wherein the herbicide comprises a herbicidally effective imidazolinone.

51. The method of claim 50, wherein the herbicide comprises imazethapyr or imazamox.

52. The method of claim 43, wherein the herbicide comprises a herbicidally effective sulfonylurea.

* * * * *